United States Patent
Gordon et al.

(10) Patent No.: US 8,556,972 B2
(45) Date of Patent: Oct. 15, 2013

(54) MONOLITHIC ORTHOPEDIC IMPLANT WITH AN ARTICULAR FINISHED SURFACE

(75) Inventors: Jeffrey D. Gordon, Cameron Park, CA (US); Michael G. Fisher, Reno, NV (US); Paul R. Johnson, Fairport, NY (US); Kenneth D. Johannaber, Rancho Murieta, CA (US)

(73) Assignee: Sevika Holding AG, Baar (CH)

( * ) Notice: Subject to any disclaimer, the term of this patent is extended or adjusted under 35 U.S.C. 154(b) by 384 days.

(21) Appl. No.: 12/829,095

(22) Filed: Jul. 1, 2010

(65) Prior Publication Data

US 2010/0268337 A1   Oct. 21, 2010

Related U.S. Application Data

(63) Continuation-in-part of application No. 12/417,374, filed on Apr. 2, 2009.

(51) Int. Cl.
*A61F 2/02* (2006.01)

(52) U.S. Cl.
USPC ............... 623/16.11; 623/23.56; 623/23.76

(58) Field of Classification Search
USPC ..................... 623/23.72–76, 16.11
See application file for complete search history.

(56) References Cited

U.S. PATENT DOCUMENTS

| | | | |
|---|---|---|---|
| 3,992,725 A | 11/1976 | Homsy | |
| 4,000,525 A | 1/1977 | Klawitter | 3/1.911 |
| 4,158,684 A | 6/1979 | Klawitter | 264/43 |
| 4,659,331 A | 4/1987 | Matthews et al. | 623/20 |
| 4,778,473 A | 10/1988 | Matthews et al. | 623/20 |
| 4,790,851 A | 12/1988 | Suire et al. | 623/16 |
| 5,258,030 A | 11/1993 | Wolfarth et al. | |
| 5,413,608 A | 5/1995 | Keller | 623/20 |
| 5,490,854 A | 2/1996 | Fisher et al. | 606/88 |
| 5,534,033 A | 7/1996 | Simpson | |
| 5,632,745 A | 5/1997 | Schwartz | 606/75 |
| 5,683,466 A | 11/1997 | Vitale | 623/18 |
| 5,702,401 A | 12/1997 | Shaffer | 606/102 |
| 5,771,310 A | 6/1998 | Vannah | 382/154 |
| 5,782,835 A | 7/1998 | Hart et al. | 606/79 |
| 6,013,104 A | 1/2000 | Kampner | 623/23 |
| 6,027,743 A | 2/2000 | Khouri et al. | 424/423 |
| 6,037,519 A | 3/2000 | McKay | 623/16 |
| 6,096,084 A | 8/2000 | Townley | 623/23.12 |

(Continued)

FOREIGN PATENT DOCUMENTS

| | | |
|---|---|---|
| WO | 96/40020 | 12/1996 |
| WO | 99/20208 | 4/1999 |

(Continued)

OTHER PUBLICATIONS

U.S. Appl. No. 12/417,374, filed Apr. 2, 2009, Gordon.

(Continued)

*Primary Examiner* — Thomas J Sweet
*Assistant Examiner* — Christopher D Prone
(74) *Attorney, Agent, or Firm* — Dorsey & Whitney LLP

(57) ABSTRACT

A monolithic material including a first region having a first variability of strength and a second region joined to the first region, the second region having a second variability of strength, wherein the monolithic material has a variability of strength less than the first variability of strength of the first region and less than the second variability of strength of the second region.

22 Claims, 17 Drawing Sheets

(56) References Cited

U.S. PATENT DOCUMENTS

| | | | |
|---|---|---|---|
| 6,398,815 B1 | 6/2002 | Pope et al. .................. 623/23.6 |
| 6,520,964 B2 | 2/2003 | Tallarida et al. | |
| 6,551,355 B1 | 4/2003 | Lewandrowski et al. .. 623/16.11 |
| 6,607,557 B1 | 8/2003 | Brosnahan et al. ........ 623/17.11 |
| 6,626,945 B2 | 9/2003 | Simon ........................ 623/17.19 |
| 6,626,950 B2* | 9/2003 | Brown et al. ............. 623/23.72 |
| 6,632,246 B1 | 10/2003 | Simon ........................ 623/14.12 |
| 6,679,917 B2 | 1/2004 | Ek ............................... 623/20.14 |
| 6,685,987 B2 | 2/2004 | Shetty ........................... 427/226 |
| 6,790,233 B2 | 9/2004 | Brodke et al. ............. 623/11.16 |
| 6,814,757 B2 | 11/2004 | Kopylov et al. ............ 623/21.11 |
| 6,846,327 B2 | 1/2005 | Khandkar et al. .......... 623/16.11 |
| 6,852,125 B2 | 2/2005 | Simon ........................ 623/16.11 |
| 6,858,042 B2* | 2/2005 | Nadler et al. .............. 623/11.11 |
| 6,881,229 B2 | 4/2005 | Khandkar et al. .......... 623/23.56 |
| 7,029,479 B2 | 4/2006 | Tallarida et al. .............. 606/102 |
| 7,270,682 B2 | 9/2007 | Frigg |
| 7,537,614 B2 | 5/2009 | Baumgartner ............. 623/17.15 |
| 7,578,851 B2 | 8/2009 | Dong et al. ................. 623/22.21 |
| 7,597,713 B2 | 10/2009 | Baumgartner et al. .... 623/17.15 |
| 2001/0039455 A1* | 11/2001 | Simon et al. ............... 623/23.51 |
| 2002/0055783 A1* | 5/2002 | Tallarida et al. ............ 623/20.14 |
| 2003/0074081 A1 | 4/2003 | Ayers ........................... 623/23.5 |
| 2003/0114936 A1 | 6/2003 | Sherwood ................. 623/23.76 |
| 2004/0107000 A1 | 6/2004 | Felt et al. |
| 2004/0175408 A1 | 9/2004 | Chun et al. .................... 424/422 |
| 2005/0049706 A1 | 3/2005 | Brodke et al. |
| 2005/0107888 A1 | 5/2005 | Khandkar et al. .......... 623/23.39 |
| 2005/0177118 A1* | 8/2005 | Hoganson et al. ....... 604/288.01 |
| 2005/0234560 A1 | 10/2005 | Serbousek et al. ......... 623/23.23 |
| 2006/0198939 A1 | 9/2006 | Smith et al. .................... 427/2.1 |
| 2006/0271201 A1 | 11/2006 | Kumar et al. ................ 623/23.5 |
| 2006/0276906 A1 | 12/2006 | Hoag et al. ................. 623/23.34 |
| 2007/0073409 A1 | 3/2007 | Cooney, III et al. ....... 623/20.11 |
| 2007/0083267 A1 | 4/2007 | Miz et al. |
| 2007/0086078 A1 | 4/2007 | Hagood et al. |
| 2007/0113951 A1 | 5/2007 | Huang ........................ 623/14.12 |
| 2007/0179608 A1 | 8/2007 | Ek et al. ..................... 623/14.12 |
| 2007/0233264 A1 | 10/2007 | Nycz .......................... 623/23.48 |
| 2008/0046091 A1 | 2/2008 | Weiss et al. ................ 623/22.37 |
| 2008/0114465 A1* | 5/2008 | Zanella et al. ............... 623/23.6 |
| 2008/0172125 A1 | 7/2008 | Ek ............................... 623/14.12 |
| 2009/0276056 A1 | 11/2009 | Bose et al. |
| 2010/0023126 A1 | 1/2010 | Grotz |

FOREIGN PATENT DOCUMENTS

| | | |
|---|---|---|
| WO | 99/60956 | 12/1999 |
| WO | 00/49977 | 8/2000 |
| WO | 01/17464 | 3/2001 |
| WO | 03/047470 | 6/2003 |
| WO | 2004/019828 | 3/2004 |
| WO | 2004/026186 | 4/2004 |
| WO | 2004/054479 | 7/2004 |

OTHER PUBLICATIONS

Rajendra S. Bhatnagar, et al., "Design of Biomimetic Habitats for Tissue Engineering with P-15, a Synthetic Peptide Analogue of Collagen," Tissue Engineering, vol. 5, No. 1, 1999, p. 53 (Abstract).

Kirker-Head et al., "Safety of, and Biological and Functional Response to, a Novel Metallic Implant for the Management of Focal Full-Thickness Cartilage Defects: Preliminary Assessment in an Animal Model Out to 1 Year", Journal of Orthopaedic Research, pp. 1095-1108.

International Search Report and Written Opinion for PCT Application No. PCT/US2009/058831, mailed May 17, 2010.

International Search Report and Written Opnion in PCT Application No. PCT/US2011/033825, dated Jan. 18, 2012.

Internationcal Search Report and Written Opinion for PCT Application No. PCT/US2011/033827, mailed Jan. 17, 2012.

* cited by examiner

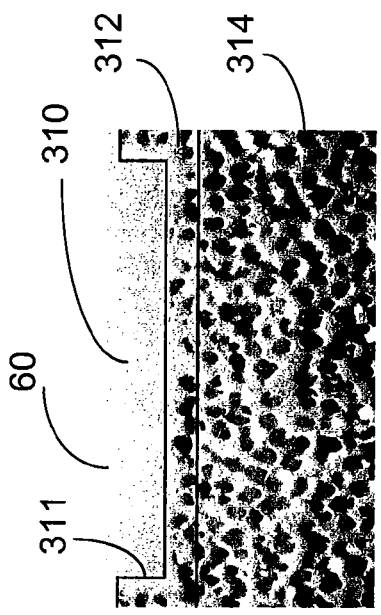
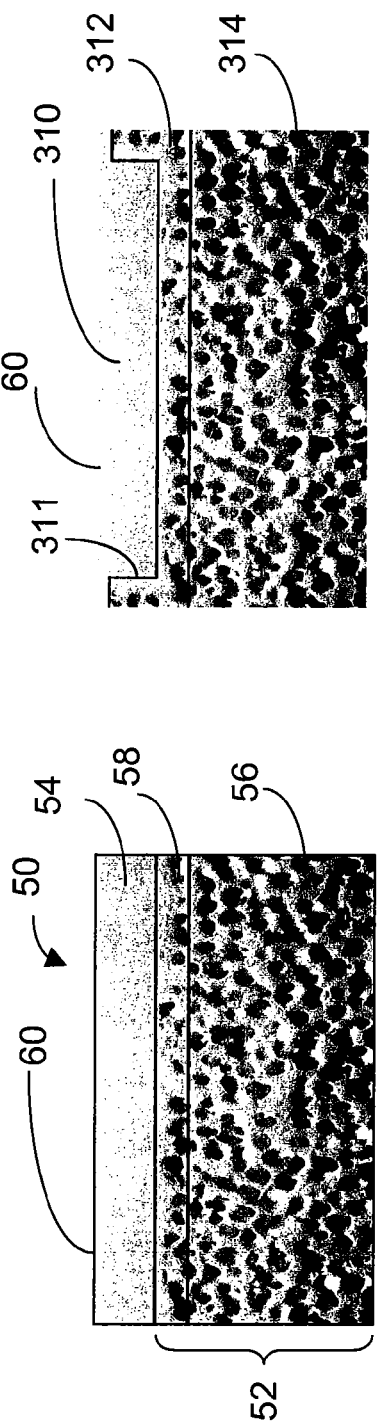
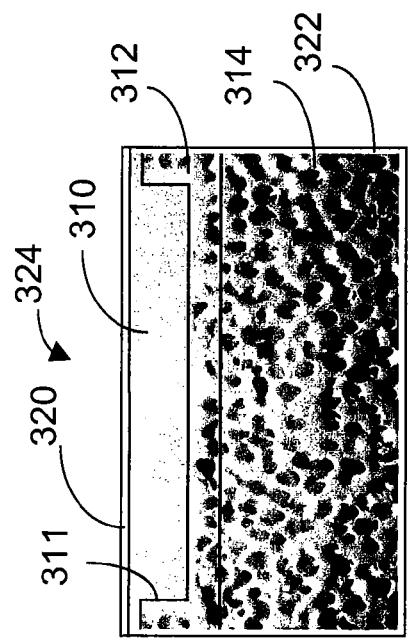

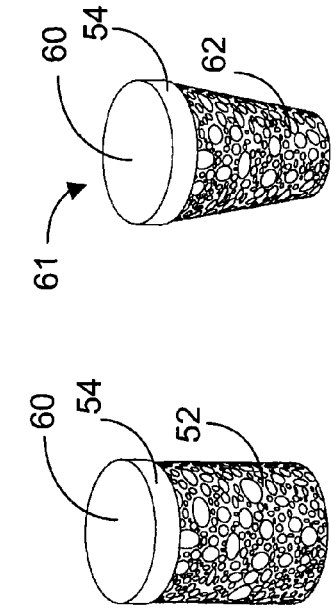
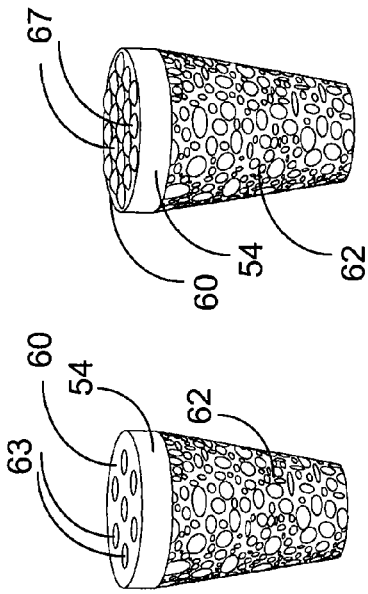
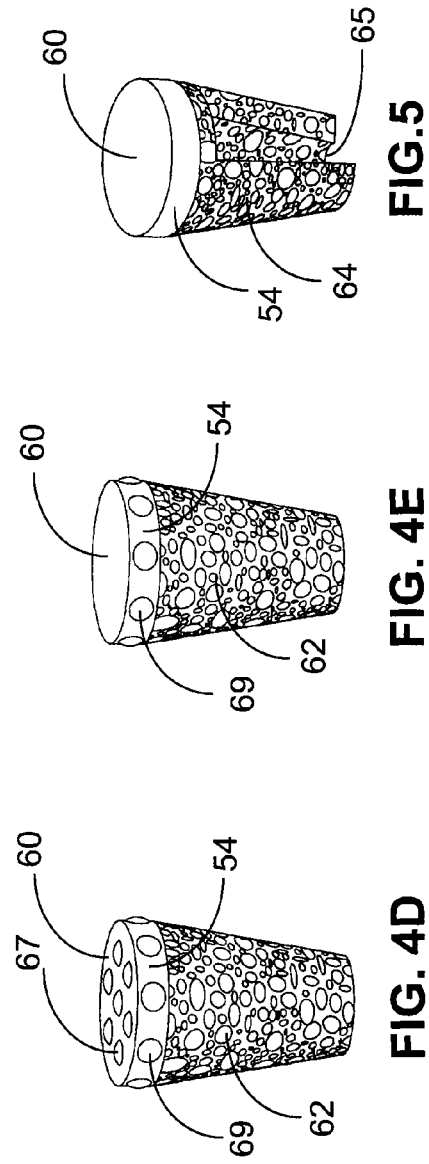
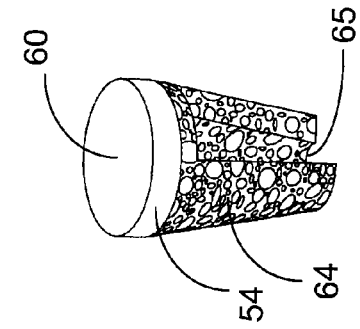

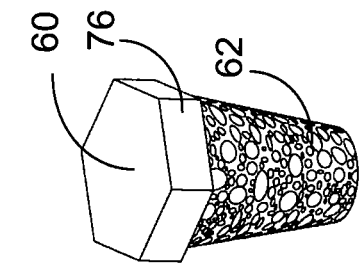
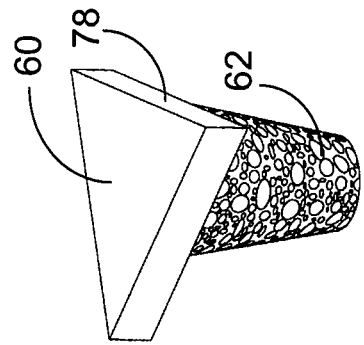
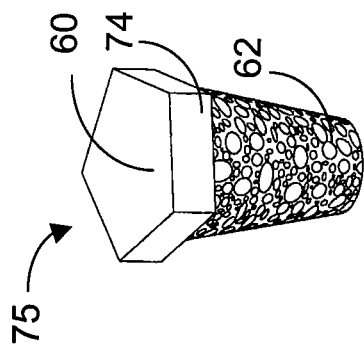
FIG. 8A
FIG. 8B
FIG. 8C

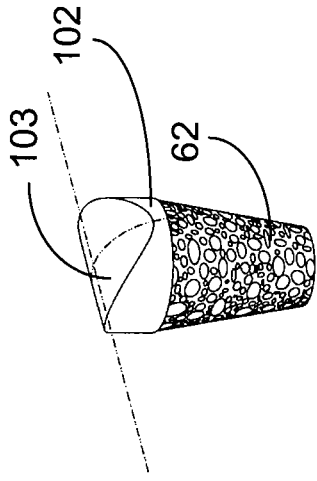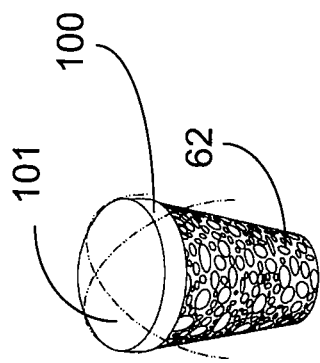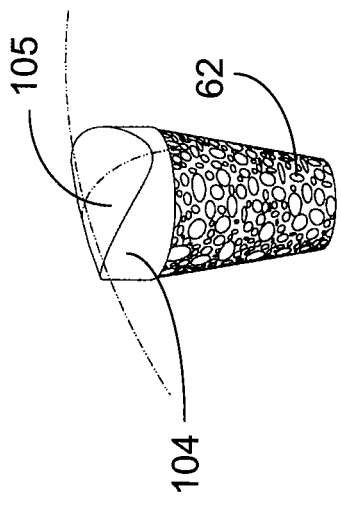
FIG. 12B
FIG. 12A
FIG. 12C

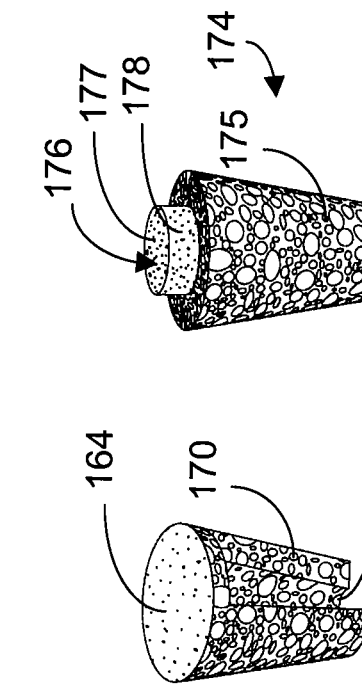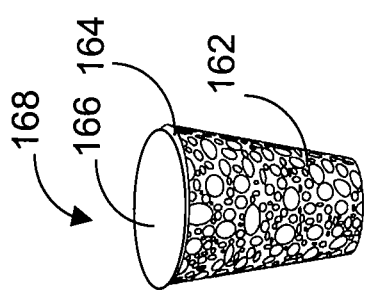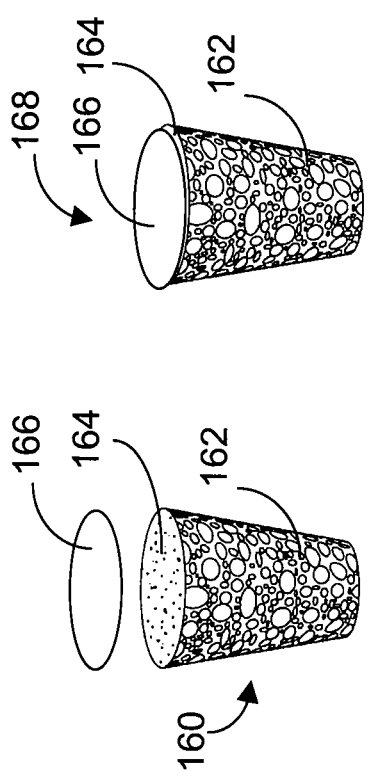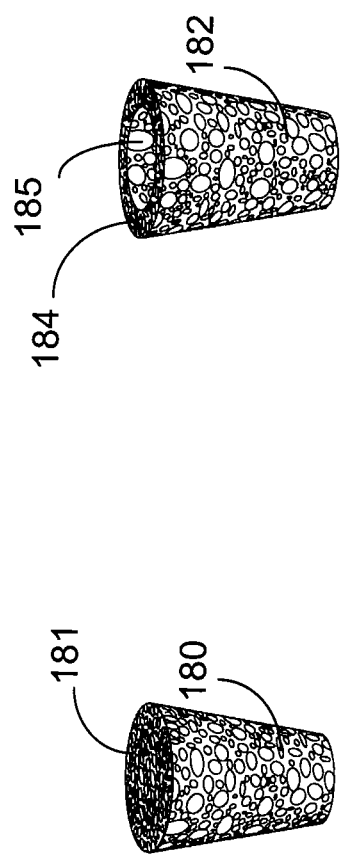
FIG. 15A  FIG. 15B  FIG. 15C  FIG. 15D
FIG. 16A  FIG. 16B

| FORMING A POROUS REGION HAVING A FORM OF INTERCONNECTED POROSITY ADAPTED TO BE SIMILAR TO CANCELLOUS BONE TO PROMOTE SKELETAL FIXATION BY BONE INGROWTH OF CANCELLOUS BONE | 200 |

| FORMING A TRANSITION REGION ADJACENT TO AND INTEGRALLY JOINED TO THE POROUS REGION, THE TRANSITION REGION HAVING A FORM OF INTERCONNECTED POROSITY ADAPTED TO BE SIMILAR TO SUBCHONDRAL BONE | 202 |

| FORMING A SUBSTANTIALLY DENSE REGION INTEGRALLY JOINED TO THE TRANSITION REGION | 204 |

| FORMING A SURFACE ON THE SUBSTANTIALLY DENSE REGION, THE SURFACE HAVING A FINISH ADAPTED FOR ARTICULATION AGAINST NATIVE ARTICULAR CARTILAGE | 206 |

| WHEREIN THE POROUS REGION HAS A POROSITY GRADIENT THAT INCREASES AS A DISTANCE FROM THE SUBSTANTIALLY DENSE REGION INCREASES | 208 |

| WHEREIN THE POROUS REGION, THE TRANSITION REGION AND THE SUBSTANTIALLY DENSE REGION ARE NONRESORBABLE | 210 |

| WHEREIN FORMING THE SURFACE COMPRISES THERMAL PROCESSING, OR COATING OR DEPOSITING A MATERIAL | 212 |

FIG. 17

| |
|---|
| REMOVING A PORTION OF THE ARTICULAR CARTILAGE AT AN IMPLANT SITE, FORMING A SOCKET IN BONE UNDERLYING THE ARTICULAR CARTILAGE, AND IMPLANTING A MONOLITHIC ORTHOPEDIC IMPLANT INTO THE SOCKET — 220 |
| THE MONOLITHIC ORTHOPEDIC IMPLANT INCLUDING A POROUS REGION HAVING A FORM OF INTERCONNECTED POROSITY ADAPTED TO BE SIMILAR TO CANCELLOUS BONE TO PROMOTE SKELETAL FIXATION BY BONE INGROWTH, A TRANSITION REGION CONNECTED TO THE POROUS REGION AND HAVING A FORM OF INTERCONNECTED POROSITY ADAPTED TO BE SIMILAR TO SUBCHONDRAL BONE, A SUBSTANTIALLY DENSE REGION INTEGRALLY JOINED TO THE TRANSITION REGION, AND A SURFACE ON THE SUBSTANTIALLY DENSE REGION, THE SURFACE HAVING A FINISH ADAPTED FOR ARTICULATION AGAINST NATIVE ARTICULAR CARTILAGE — 222 |
| WHEREIN THE POROUS REGION HAS A POROSITY GRADIENT THAT INCREASES AS A DISTANCE FROM THE SUBSTANTIALLY DENSE REGION INCREASES — 224 |
| WHEREIN THE POROUS REGION, THE SUBSTANTIALLY DENSE REGION, AND THE SURFACE ARE NON-RESORBABLE — 226 |
| WHEREIN THE POROUS REGION, THE SUBSTANTIALLY DENSE REGION, AND THE SURFACE COMPRISE CERAMIC. — 228 |

FIG. 18A

IMPLANTING A PLURALITY OF MONOLITHIC ORTHOPEDIC
IMPLANTS ADJACENT TO ONE ANOTHER TO CREATE A    232
NEARLY CONTINUOUS ARTICULAR SURFACE

WHEREIN THE SUBSTANTIALLY DENSE REGION OF EACH
MONOLITHIC ORTHOPEDIC IMPLANT HAS A POLYGON
SHAPED PERIMETER.                               234

FIG. 18B

FORMING A POROUS REGION HAVING A FIRST VARIABILITY OF STRENGTH — 240

FORMING A SUBSTANTIALLY DENSE REGION JOINED TO THE POROUS REGION AND HAVING A SECOND VARIABILITY OF STRENGTH, WHEREIN THE VARIABILITY OF STRENGTH OF THE MONOLITHIC MATERIAL IS LESS THAN THE FIRST AND SECOND VARIABILITY OF STRENGTHS — 242

FORMING A TRANSITION REGION BETWEEN THE POROUS REGION AND THE SUBSTANTIALLY DENSE REGION AND JOINED TO THE POROUS REGION AND THE SUBSTANTIALLY DENSE REGION, THE TRANSITION REGION HAVING A THIRD VARIABILITY OF STRENGTH, WHEREIN THE VARIABILITY OF STRENGTH OF THE MONOLITHIC MATERIAL IS LESS THAN THE THIRD VARIABILITY OF STRENGTH — 244

FORMING A SURFACE ON THE SUBSTANTIALLY DENSE REGION, THE SURFACE HAVING A FINISH ADAPTED FOR ARTICULATION AGAINST NATIVE ARTICULAR CARTILAGE — 246

FIG. 19

```
FORMING A FIRST REGION HAVING A FIRST VARIABILITY
OF STRENGTH                                         250
```

```
FORMING A SECOND REGION JOINED TO THE FIRST    252
REGION, THE SECOND REGION HAVING A SECOND
VARIABILITY OF STRENGTH, WHEREIN THE MONOLITHIC
MATERIAL HAS A VARIABILITY OF STRENGTH LESS THAN
THE FIRST VARIABILITY OF STRENGTH OF THE FIRST
REGION AND LESS THAN THE SECOND VARIABILITY OF
STRENGTH OF THE SECOND REGION
```

```
FORMING A THIRD REGION BETWEEN AND JOINED TO THE
FIRST REGION AND THE SECOND REGION, THE THIRD   254
REGION HAVING A THIRD VARIABILITY OF STRENGTH,
WHEREIN THE VARIABILITY OF STRENGTH OF THE
MONOLITHIC MATERIAL IS LESS THAN THE THIRD
VARIABILITY OF STRENGTH OF THE THIRD REGION
```

FIG. 20

MONOLITHIC ORTHOPEDIC IMPLANT WITH AN ARTICULAR FINISHED SURFACE

CROSS REFERENCE TO RELATED APPLICATIONS

This application is a continuation in part of U.S. patent application Ser. No. 12/417,374, filed Apr. 2, 2009, which is incorporated herein by reference as though set forth in full.

FIELD

This disclosure relates to orthopedic implants and in particular to orthopedic implants for repair of focal articular cartilage and osteochondral defects.

BACKGROUND

As the population of an active society ages, medical advancements are developed to improve the health of individuals. One of the most active and successful medical treatments is joint reconstruction, also known as arthroplasty, to resolve activity limiting pain caused by arthritis. Current technology supports various forms of arthroplasty, including hemi-arthroplasty, partial joint arthroplasty and total joint arthroplasty. These successful procedures reconstruct a new continuous, low friction articular surface for pain free function of the skeletal joint. A remaining challenge in arthroplasty deals with resolving activity limiting pain in patients with smaller focal cartilage lesions. These lesions represent earlier stages of arthritis and if left untreated potentially progress to later stages of arthritis requiring a more invasive procedure such as partial or total joint replacement. The current challenge in treating arthritis lies in developing a more versatile implant for focal, regional or global resurfacing that successfully interacts with mating articular cartilage, surrounding articular cartilage and the underlying bone bed.

Diarthrodial joints in the human skeleton provide the nearly frictionless pain free movement supporting locomotion, spatial positioning relative to the environment and active manipulation of the surroundings. These skeletal joints have a strong fibrous capsule enclosing bone ends encapsulated by smooth continuous cartilage surfaces to accomplish this function. This biologic configuration represents the majority of skeletal joints in the human body.

The encapsulating surface on the ends of moving bones is known as hyaline cartilage, a hydrated soft tissue comprised of collagen, trapped proteoglycans, other proteins and chondrocytes. This tissue is more commonly known as articular cartilage or native articular cartilage. This ordered tissue provides a resilient, continuous layer of protective tissue on the bone ends. In addition to protecting the bone ends, it also helps develop an extraordinarily low coefficient of friction during joint movement, by interacting with the synovial fluid.

The resiliency of articular cartilage is supported by a dense bone layer, called the subchondral plate, which provides foundational strength for the articular cartilage. The bone side of the subchondral plate is supported by cancellous bone. Cancellous bone is a highly porous structure with a stiffness $1/10^{th}$ that of the subchondral plate. The cancellous bone acts to distribute loads across the joint in the metaphyseal region of bone ends.

Skeletal joints are subject to wear and tear though use, trauma and aging. These factors eventually cause biologic changes to the articular cartilage resulting in arthritis, a group of progressive conditions ultimately resulting in irreversible damage to the articular cartilage in skeletal joints.

As damage to the affected articular cartilage surfaces progress, the smooth continuous layer of protective tissue becomes torn and discontinuous. Unlike other tissues, the body is unable to regenerate this well ordered hyaline cartilage and substitutes a less durable, rougher form of cartilage known as fibrocartilage. This less protective fibrocartilage increases the coefficient of friction in the joint and results in a greater volume of microfracturing in the cancellous bone. In reaction to this structural breakdown, the body reacts by thickening the subchondral plate to assist in distributing the load across the bone end. Researchers have sighted this stiffening of the subchondral bone as a possible mechanism for the initiation of cartilage damage. This may be why untreated cartilage lesions cause arthritis to progress and affect larger areas of articular cartilage in a joint over time, leading to activity limiting pain and decreased joint function.

Osteoarthritis (OA) or Degenerative Joint Disease (DJD) is the most common form of arthritis and presents the patient with debilitating pain during daily activities. It is the leading cause of chronic disability in the United States in the middle-aged population, but affects people of all ages. It is estimated that 21 million people have a form of arthritis in the US, accounting for 25% of visits to primary care physicians and half of all NSAID (Non-Steroidal Anti-Inflammatory Drugs) prescriptions.

OA commonly affects the joints at the hips, knees, shoulder, elbow and spine, and small joints such as those found in the hands and feet. As a result, various methods have been developed to treat and repair damaged or destroyed articular cartilage.

For smaller defects, usually identified early in the onset of arthritis during diagnostic workups, arthroscopic debridement, abrasion arthroplasty or abrasion chondralplasty procedures are conducted. The principle behind these procedures is to stimulate bleeding of the subchondral bone bed by abrading it with a burr or shaver to stimulate the fibrocartilage healing response. Although this procedure has been widely used over the past two decades, with good short term results out to three years, the resulting fibrocartilage developed in the healed area does not always support longer term low friction weight bearing function.

Another procedure referred to as "microfracture" incorporates the concept of fibrocartilage healing by removing the damaged cartilage layer and using a surgical awl to perforate the subchondral bone. This technique creates a replacement surface similar in type and outcome to the one created from the abrasion chondralplasty technique.

Transplantation of previously harvested hyaline cartilage cells, known as cell-based therapy, has been utilized in recent years. This technique uses autologous chondrocytes obtained from a specimen of articular cartilage obtained from an uninvolved area of the injured joint. The cartilage cells are isolated, cultured and implanted in the defect area under a periosteal flap. Compared to the previously discussed abrasion techniques, this procedure requires a lengthy post-operative non-weight bearing course and is still viewed somewhat as experimental because of the technical challenges involved in the procedure producing variations in patient outcomes.

Cartilage transplant, referred to as Mosaicplasty or Osteoarticular Transfer System (OATS) is a technique utilizing articular tissue grafts in the form of plugs. These plugs consist of articular cartilage, subchondral bone and cancellous bone to assure they heal to the bone and surrounding articular cartilage in the surgically prepared defect region.

Two different types of donor plugs are harvested for this procedure. The first is taken from a matched articular location in a cadaver bone (allograft). The second type is taken directly from the patient (autograft) in boundary or non-weight bearing locations in the joint being reconstructed.

In either case, the technique for utilizing articular cartilage grafts is challenging. Success of the technique requires accurate harvesting and positioning of single or multiple plugs to reconstruct the articular surface of the subject joint. The plug must be harvested perpendicular to the articular surface, then positioned perpendicular and flush with the retained articular cartilage surrounding the defect area. If the grafts are placed too far below the level of the surrounding articular surface, no benefit from the procedure will be gained and cartilage damage can progress beyond the perimeter of the original defect. If the grafts are placed proud to the surrounding articular surface, detrimental effects can be seen on the mating articular surface over time in the joint. This is important to consider since arthritis often affects one side of an articular joint first before progressing to the mating surface.

The result of positioning these plugs in a mosaic-like fashion establishes a new hyaline cartilage surface. The result is a hyaline-like surface interposed with a fibrocartilage healing response between each graft. In addition to the many challenges discussed surrounding this procedure, a lengthy post-operative non-weight bearing course is required to improve the patient's chance for success in restoring functional articular cartilage in the skeletal joint.

Other clinical challenges exist beyond the technique issues previously discussed. In the case of allograft plugs graft availability, potential disease transmission and tissue quality are all concerns. In the case of autograft plugs, the quantity and articular shape of available tissue create limitations in the defect size to be treated.

Advances in tissue engineering are beginning to provide treatments to repair focal cartilage lesions in skeletal joints by implanting collagen based scaffold devices, with and without impregnated autologous chondrocytes (cartilage cells). This reconstructive technique, referred to as scaffold guided regeneration, establishes a generic tissue foundation which is converted over time by the body into hyaline cartilage. Initial results using this reconstructive technique show promise, but are currently used in non-weight bearing applications which limit their use in reconstructive procedures presently favoring more traditional devices made from implantable metals, ultra high molecular weight polyethylene (UHMWPE) and ceramics.

One type of joint replacement technique using more traditional devices is called hemi-arthroplasty. This reconstructive procedure replaces one bone end of the two or more bone ends comprising a skeletal joint. The procedure leaves the healthy part or parts of the joint unaltered. The challenge is for the artificial implant to articulate with the native cartilage surfaces over time without recreating painful arthritis as the healthy cartilage tissue becomes arthritic. Clinical experience in using hemi-arthroplasty implants with metal articular surfaces in younger more active patients has shown undesirable thinning and damage of the mating native articular cartilage in early term follow-up. For this reason, this class of procedure is most commonly performed in older patients following a hip fracture. During hemi-arthroplasty of the hip, the surgeon removes the damaged bone and cartilage from the hip joint, usually the femoral head. The healthy mating surface in the acetabulum or pelvis is left intact. One such implant in accordance with the prior art is shown in FIG. 1A and is further described in U.S. Pat. No. 6,096,084 to Townley. The implant 20 can be used for hemi-arthroplasty or in total arthroplasty. The implant 20 may have a ceramic head 22 and a metal stem 24, which is implanted in the proximal region of the femur. The metal stem 24 in Townley is made of cobalt chrome, which is a cobalt-chromium-molybdenum alloy, a metal alloy often used for reconstructive implants. The stem provides a means for fixing the implant to bone to stabilize the artificial articular surface. Similar devices to this hip implant are used in the shoulder, knee, ankle, hands and feet.

When arthritis progresses to all aspects of an articular joint a total joint arthroplasty is performed to reconstruct the cartilage on all bone ends making up the skeletal joint. This comprehensive procedure is required to effectively resolve the activity limiting pain caused by the arthritis. In a total knee, for example, a highly polished metal implant is placed onto the distal femur. A modular metal tray is implanted in the proximal tibia and a UHMWPE bearing joined to it to articulate with the highly polished femoral component. A UHMWPE patellar implant is placed to resurface the patella and articulate against the anterior flange of highly polished femoral implant. This completely resurfaces the femoral-tibial and patella-femoral articular surfaces in the total knee replacement.

The risks involved in joint arthroplasty described previously include mal-position of the components, skeletal loosening, instability/dislocation, loss of range of motion and recurring activity limiting pain.

One long term risk is loosening of the components, because the bond between the bone and the components or the cement may break down or fatigue. Various approaches in the prior art attempt to address the loosening risk. For example, U.S. Pat. No. 6,685,987 describes a porous coating comprised of metallic particles applied over a cobalt chromium molybdenum alloy implant.

Generally joint replacement bearing surfaces are made of cobalt chromium; however other materials have been used or proposed including titanium and titanium alloys. U.S. Patent Application Publication No. 2005/0107888 to Khandkar et al. describes a metal-ceramic composite for joint replacement materials. U.S. Pat. No. 6,398,815 to Pope et al. describes a prosthetic joint with diamond like surfaces.

As described above, the replacement with prosthetic joints is currently the preferred option for serious degeneration of joint function involving loss of articular cartilage. Other techniques include U.S. Pat. No. 7,029,479 to Tallarida et al. that discloses a method for joint resurface repair which involves mapping and measuring the articular surface, U.S. Pat. No. 5,782,835 to Hart et al. that discloses an apparatus and method for repair of articular cartilage including a bone plug removal tool, and a bone plug emplacement tool, U.S. Pat. No. 6,679,917 to Ek that discloses an implant for installation into a portion of an articular surface including a protrusion configured to cover an un-excised portion of the articular surface proximate to the implant, U.S. Pat. No. 5,413,608 to Keller that discloses a knee joint endoprosthesis for replacing the articular surfaces of the tibia comprising a bearing part that is anchored on the bone having an upper bearing surface and a rotatable plateau secured on the bearing surface and forming a part of the articular surface to be replaced, U.S. Pat. No. 5,632,745 to Schwartz that describes a method of surgically implanting into a site a bio-absorbable cartilage repair assembly, U.S. Pat. No. 5,683,466 to Vitale that discloses an articular joint surface replacement system having two opposing components, U.S. Pat. No. 5,702,401 to Shaffer that discloses an intra-articular measuring device including a hollow handle defining a first passageway and a hollow tube having a second passageway extending from the handle, and U.S. Pat. No. 5,771,310 to Vannah that describes a method of mapping the three-dimensional topography of the surface of an object by generating digital data points at a plurality of sample points on said surface. Another implant is described in U.S.

Publication No. 2003/0074081 to Ayers that describes a method for production of tissue implants and prosthetics. U.S. Publication No. 2007/0113951 to Huang describes an osteochondral composite scaffold for articular cartilage repair.

Another orthopedic procedure involves fusing bones together and is clearly distinct from joint replacement. One such application is for spinal fusion. For example U.S. Patent Application Publication No. 2005/0049706 and U.S. Pat. No. 6,790,233 to Brodke et al. describe radio lucent spinal fusion cages, one of which is shown in FIG. 1B. The cage includes a substrate block 30 having a high bio-mechanical strength and load bearing capacity to support the spinal vertebrae 32 and a porous silicon nitride ceramic portion 34 to promote bone ingrowth and fusion. Other examples of fusing bones together include U.S. Patent Application Publication No. 2006/0271201 to Kumar et al. that describes using porous ceramic 36 to repair defects in bone 38, as shown in FIG. 1C, and U.S. Pat. No. 6,607,557. Because these devices are intended to fuse bones together, they are inappropriate for repair of damaged joints which by their nature should have free movement.

The reconstructive prior art methods for articular cartilage repair previously discussed have disadvantages and drawbacks related to treating early stage arthritis to prevent progression to a more final stage requiring total joint replacement.

What is needed is a more versatile articular orthopedic implant to function in a collaborative environment with native tissue. Also needed is a non-resorbable implant to support loads imposed by an opposing joint end. In particular what is needed is an implant that will facilitate surgical repair of focal, regional and global articular cartilage and osteochondral defects on a bone end of a skeletal joint to prevent or delay the global progression of arthritis to the entire joint. The embodiments of the present disclosure answer these and other needs.

SUMMARY

In a first embodiment disclosed herein, a monolithic orthopedic implant includes a porous region having a form of interconnected porosity similar to cancellous bone to promote skeletal fixation by bone ingrowth, a transition region adjacent to and integrally joined to the porous region, the transition region having a form of interconnected porosity similar to subchondral bone, a substantially dense region integrally joined to the transition region and having a perimeter, and a surface on the substantially dense region, the surface having a finish adapted for articulation against native articular cartilage.

In another embodiment disclosed herein, an orthopedic implant comprises a porous region having a form of interconnected porosity similar to cancellous bone to promote skeletal fixation by bone ingrowth, and a transition region adjacent to and integrally joined to the porous region, the transition region having a form of porosity similar to subchondral bone, wherein the transition region is adapted to promote regeneration of articular cartilage, and wherein the porous region and the transition region are non-resorbable.

In another embodiment disclosed herein, a dental implant comprises a porous region having a form of interconnected porosity similar to cancellous bone to promote skeletal fixation by bone ingrowth, and a substantially dense region integrally joined to the porous region, the substantially dense region having a top surface and a perimeter, wherein the top surface and the perimeter are adapted to be compatible with oral gum tissue, and wherein the porous region and the substantially dense region are non-resorbable.

In another embodiment disclosed herein, a method of forming a monolithic orthopedic implant includes forming a porous region having a form of interconnected porosity similar to cancellous bone to promote skeletal fixation by bone ingrowth, forming a transition region adjacent to and integrally joined to the porous region, the transition region having a form of interconnected porosity similar to subchondral bone, forming a substantially dense region integrally joined to the transition region and having a perimeter, and forming a surface on the substantially dense region, the surface having a finish adapted for articulation against native articular cartilage, wherein the porous region has a porosity gradient that increases as a distance from the substantially dense region increases, and wherein the porous region, the transition region and the substantially dense region are non-resorbable.

In yet another embodiment disclosed herein, a method for orthopedic surgery includes removing a portion of the articular cartilage at an implant site, forming a socket in bone underlying the articular cartilage to a depth placing the surface of the substantially dense region of the monolithic implant approximately flush to the articular cartilage at the implant site, and implanting a monolithic orthopedic implant into the socket, the monolithic orthopedic implant comprising a porous region having a form of interconnected porosity similar to cancellous bone to promote skeletal fixation by bone ingrowth, a transition region adjacent to and integrally joined to the porous region, the transition region having a form of interconnected porosity similar to subchondral bone, a substantially dense region integrally joined to the transition region, and a surface on the substantially dense region, the surface having a finish adapted for articulation against native articular cartilage, wherein the porous region, the transition region, the substantially dense region, and the surface are non-resorbable.

In yet another embodiment disclosed herein, an orthopedic implant comprises a three dimensional framework of structural members with interstitial interconnected passages there between, wherein the structural members comprise non-resorbable ceramic, and wherein each structural member is similar in size to a trabecula in bone.

In an embodiment disclosed herein, a monolithic material comprises a first region having a first variability of strength, and a second region joined to the first region, the second region having a second variability of strength, wherein the monolithic material has a variability of strength less than the first variability of strength of the first region and less than the second variability of strength of the second region.

In another embodiment disclosed herein, a monolithic orthopedic implant comprises a porous region having a first variability of strength, a transition region integrally joined to the porous region and having a second variability of strength, a substantially dense region integrally joined to the transition region and having a third variability of strength, and a surface on the substantially dense region, the surface having a finish adapted for articulation against native articular cartilage, wherein the variability of strength of the monolithic orthopedic implant is less than the first, second, and third variability of strengths.

In yet another embodiment disclosed herein, a method of providing a monolithic material comprises forming a porous region having a first variability of strength, and forming a substantially dense region joined to the porous region and having a second variability of strength, wherein the variability of strength of the monolithic material is less than the first and second variability of strengths.

In still another embodiment disclosed herein, a method of providing a monolithic material comprises forming a first region having a first variability of strength, and forming a second region joined to the first region, the second region having a second variability of strength, wherein the monolithic material has a variability of strength less than the first variability of strength of the first region and less than the second variability of strength of the second region.

These and other features and advantages will become further apparent from the detailed description and accompanying figures that follow. In the figures and description, numerals indicate the various features, like numerals referring to like features throughout both the drawings and the description.

BRIEF DESCRIPTION OF THE DRAWINGS

FIG. 2A shows a cross section of a monolithic orthopedic implant in accordance with the present disclosure;

FIG. 2B shows cross section of another monolithic orthopedic implant in accordance with the present disclosure;

FIG. 2C shows a cross section of yet another monolithic orthopedic implant in accordance with the present disclosure;

FIG. 3 shows a perspective view of a monolithic orthopedic implant with the porous region having the shape of a cylindrical plug in accordance with the present disclosure;

FIGS. 4A-4E show perspective views of a monolithic orthopedic implant with the porous region having the shape of a tapered plug in accordance with the present disclosure. The monolithic orthopedic implants shown in FIGS. 4B-4E show protrusions or dimples on the substantially dense region in accordance with the present disclosure;

FIG. 5 shows a perspective view of a monolithic orthopedic implant with the porous region having a hollow interior in accordance with the present disclosure;

FIG. 8A shows a perspective view of a monolithic orthopedic implant with a porous region and a substantially dense region having a polygonal shape or a pentagonal shape in accordance with the present disclosure;

FIG. 8B shows a perspective view of a monolithic orthopedic implant with a porous region and a substantially dense region having a polygonal shape or a hexagonal shape in accordance with the present disclosure;

FIG. 8C shows a perspective view of a monolithic orthopedic implant with a porous region and a substantially dense region having a polygonal shape or a triangular shape in accordance with the present disclosure;

FIG. 12A shows a perspective view of a monolithic orthopedic implant with a porous region and a substantially dense region with an articular surface having a convex spherical shape to match a skeletal joint in accordance with the present disclosure;

FIG. 12B shows a perspective view of a monolithic orthopedic implant with a porous region and a substantially dense region with an articular surface having a convex shape with a radius in one plane to match a skeletal joint in accordance with the present disclosure;

FIG. 12C shows a perspective view of a monolithic orthopedic implant with a porous region and a substantially dense region with an articular surface having a convex shape with two differing radii in two planes to match a skeletal joint in accordance with the present disclosure;

FIG. 15A shows a perspective view of an orthopedic implant with a porous region and a transition region in accordance with the present disclosure.

FIG. 15B shows a scaffold coupled to the transition region of FIG. 15A in accordance with the present disclosure.

FIG. 15C shows a perspective view of an orthopedic implant with a porous region having a hollow interior and a transition region in accordance with the present disclosure.

FIG. 15D shows a perspective view of a dental implant in accordance with the present disclosure.

FIG. 16A shows a perspective view of a monolithic non-resorbable porous implant in accordance with the present disclosure;

FIG. 16B shows a perspective view of a monolithic non-resorbable porous implant having a hollow interior in accordance with the present disclosure;

FIG. 17 is a flow diagram for fabricating a monolithic orthopedic implant in accordance with the present disclosure;

FIGS. 18A and 18B are flow diagrams of a method of orthopedic surgery in accordance with the present disclosure;

FIG. 19 is a flow diagram of a method for providing a monolithic material in accordance with the present disclosure; and FIG. 20 is a flow diagram of another method for providing a monolithic material in accordance with the present disclosure.

DETAILED DESCRIPTION

Figure 1B:
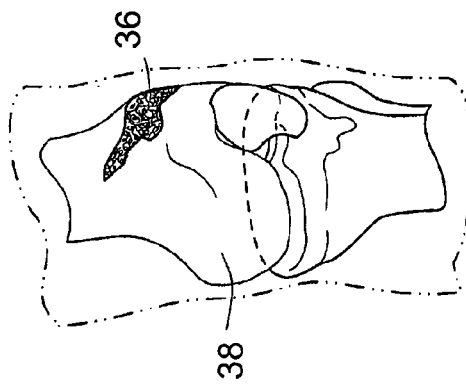
FIG. 1B shows an implant for fusing spinal vertebrae in accordance with the prior art.
Figure 1C:
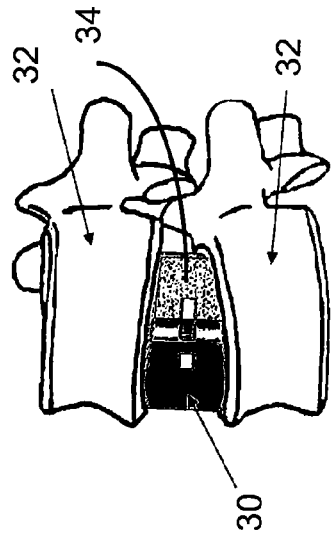
FIG. 1C shows an implant for repairing bone defects in accordance with the prior art.
Figure 1A:
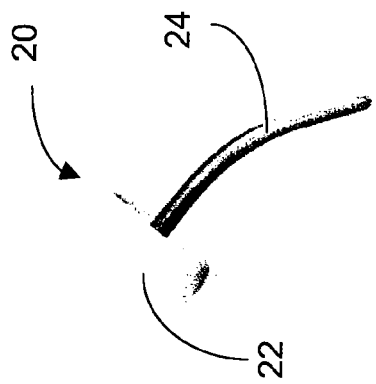
FIG. 1A shows an implant that can be used for hemiarthroplasty joint repair in accordance with the prior art.

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

Referring now to FIG. 2A, a cross section of a monolithic orthopedic implant 50 is shown which is adapted for articulating with articular cartilage in accordance with the present disclosure. In one embodiment the monolithic orthopedic implant may have a porous region 52, integrally joined to a substantially dense region 54. In order to promote skeletal fixation by bone ingrowth, the porous region 52 has a form of interconnected porosity adapted to be similar to cancellous or trabecular bone. The surface 60 of the substantially dense region 54 preferably has a finish adapted for articulation of the surface 60 against native articular cartilage on an opposing joint. The substantially dense region 54 may have a thickness that is adapted to the thickness of the native articular cartilage at the implantation site of the monolithic orthopedic implant.

In another embodiment a transition region 58 may be between a porous region 56, which as shown in FIG. 2A may be a portion of the porous region 52, and the substantially dense region 54. The porous region 56 may be adapted to have a form of interconnected porosity similar to cancellous bone. The transition region 58 may be adapted to have a form of interconnected porosity similar to subchondral bone. Thus, the monolithic orthopedic implant 50 has a porous region 56 adapted for ingrowth of cancellous bone to ensure that the monolithic orthopedic implant is securely implanted, a transition region 58 adapted to have a form of porosity similar to subchondral bone to facilitate fluid transfer similar to fluid transfer through subchondral bone, a substantially dense region 54 for bearing loads imposed by an opposing joint end, and a surface 60 on the substantially dense region 54 with a finish adapted for articulation against native articular cartilage. The thicknesses of the transition region 58 and the substantially dense region 54 may be adapted to be similar to the thicknesses of the subchondral bone and the native articular cartilage, respectively, at the implantation site for the monolithic orthopedic implant.

The substantially dense region 54 has relatively little or no porosity compared to the porous region 56 and the transition region 58. The following discusses porosity as it relates to present invention.

The bulk porosity (Pb) of a material is inversely proportional to the bulk density (Db) of the material, which can be calculated by dividing the total mass (Mtot) by the total volume (Vtot), where the mass and volume of a solid portion of the material and a porous portion of the material are designated by (Ms, Vs) and (Mp, Vp), respectively:

$$Db=(Mtot)/(Vtot)=(Ms+Mp)/(Vs+Vp), \quad (1)$$

and because the mass of porous portion of a material can be considered to be zero, equation 1 can be rewritten as:

$$Db=(Mtot)/(Vtot)=(Ms)/(Vs+Vp). \quad (2)$$

Thus, the bulk porosity (Pb) of a material is therefore:

$$Pb \sim 1/Db=(Vs+Vp)/Ms. \quad (3)$$

The porosity that may be most deleterious to a surface having a finish adapted for articulation against native articular cartilage, such as surface 60, is porosity with pores connected to the material surface. A material with substantial porosity is generally not appropriate for surface 60, because there can be material breakage under and at the edges of pores of such a material. It is also more difficult to polish porous materials, because coarser abrasive particles from early stages of grinding and polishing can become trapped in the pores, and then the particles can escape during polishing and finishing, which causes unwanted scratches and surface damage.

On the other hand, open and interconnected pores are preferable for promoting bone ingrowth.

The monolithic orthopedic implant of the present disclosure solves this contradiction in desired properties by providing the porous region 56 with a form of interconnected porosity of a form similar to cancellous bone, the transition region 58 with a form of interconnected porosity similar to subchondral bone, and the substantially dense region 54 with relatively little if any porosity, which are all integrally joined to form the monolithic orthopedic implant 50. In one embodiment the substantially dense region 54 may have a bulk porosity of 4% or less, and in another embodiment the bulk porosity of the substantially dense region 54 may be 0.1% or less. The porous region 56 may have a bulk porosity of 50% or greater. The transition region 58 has an interconnected porosity that is relatively lower than the porous region 56 to provide strength while supporting capillary movement of fluid between the cancellous bone and articular cartilage. The result is an orthopedic implant 50 that provides a scaffold for bone ingrowth and fluid communication between the cancellous bone and cartilage, while providing strength and a surface that can be finished for articulation against native articular cartilage.

In the following the porous region is referred to as porous region 56, although it should be understood that in the following reference to a porous region may also refer to the porous region 52, which includes the porous region 56 and the transition region 58.

The monolithic orthopedic implant 50 is preferably non-resorbable. Thus, the porous region 56, the transition region 58, and the substantially dense region 54 are not resorbed or converted into a specific tissue type by the body and do not lose any substance over time when implanted in a skeletal joint location. This avoids a disadvantage of many prior art implants, because in some of those implants the biologic timing of this resorption or conversion happens relatively quickly causing cyst formation and a loss of structural support for the articular cartilage, a clearly undesirable phenomenon.

The dividing line between the porous region 56 and the transition region 58, shown in FIG. 2A, may be somewhat arbitrary as the porous region 56 may gradually change into the transition region 58.

The porous region 56, and also the transition region 58 may have porosity gradients that increase as a distance from the substantially dense region 54 increases. In general the porous region 56 may be described as having a three dimensional framework with interconnected structural members with interstitial interconnected passages between the structural members. Each structural member may be similar in size to a trabecula in bone. This structure allows fluid to flow through the porous region 56 which provides for cell transfer that encourages and sustains bone ingrowth. As discussed above, the structure of the transition region 58 is adapted to have a form of porosity similar to subchondral bone, which facilitates capillary movement of fluid between the cancellous bone and articular cartilage.

In one embodiment the porous region 56 has interconnected pore passageways each with a dimension less than 1000 micrometers to promote bone ingrowth. In another embodiment the porous region 56 has interconnected pore passageways each with a dimension between 200 micrometers and 600 micrometers to promote bone ingrowth.

The porous region 56 may be further adapted to promote bone ingrowth for bone fixation. In one embodiment the porous region 56 has a roughness, characterized by a frictional coefficient similar to cancellous bone, which is generally greater than 0.5. The frictional coefficient is a biomechanical characterization of friction between cancellous bone and cortical bone. The frictional coefficient of the porous region 56 helps prevent the formation of a fibrous layer, which can retard bone ingrowth. The roughness may be on the outside of the porous region 56 and also on the inside of the porous region 56. The porous region 56 is preferably a three dimensional framework of interconnected structural members with interstitial interconnected passages there between and the roughness may be on the structural members, which provides a microstructure to promote bone ingrowth and fixation by facilitating cell adhesion. Each structural member may be similar in size to a trabecula in bone.

In another embodiment the porous region 56 has a hydrophilic or a charged surface that can influence a cell population to enhance bone ingrowth for bone fixation. These surface modifications have been shown to attract a cell population and/or influence the organization of cells to enhance healing of the surrounding native articular cartilage.

In yet another embodiment the porous region 56 may include a bioactive mineral coating, which may be hydroxyapatite, bioglass, or a form of calcium phosphate, nonlimiting examples of which are tri-calcium phosphate (TCP), alpha TCP, or beta TCP, or any combination thereof to promote bone ingrowth for bone fixation.

In still another embodiment the porous region 56 may include a bioengineered coating to promote bone ingrowth for bone fixation. The bioengineered coating may consist of one or more proteins, a peptide, or any combination thereof. An example of a peptide is a synthetic peptide analogue of collagen designed to create biomimetic cell binding habitats. Examples of proteins that can be used include the family of bone morphogenetic proteins, known as BMP's.

The surface 60 on the substantially dense region 54 may be finished to a surface roughness of 6 micrometers $R_a$ or less for articulation with articular cartilage on an opposing joint. The 6 micrometers $R_a$ or less surface roughness provides a smooth surface for opposing articulating cartilage in a joint to ride or bear upon, which avoids the wear and eventual tearing of the articulating cartilage that would occur if the surface roughness were high, especially if the surface had open pores. In one embodiment, the surface roughness is less than 0.025 micrometers Ra.

The porous region 56, the transition region 58, and the substantially dense region 54 may have the same material composition. For example, in one embodiment the monolithic orthopedic implant 50 may be entirely made of ceramic. Partially stabilized zirconia is a preferred material for the entire monolithic orthopedic implant 50. In another embodiment the porous region 56, the transition region 58, and the substantially dense region 54 are composed of different material compositions, and in this embodiment the transition region 58 may have a composition that is a mix of the composition of the porous region 56 and the composition of the substantially dense region 54.

FIG. 2B shows a cross section of another embodiment of a monolithic orthopedic implant having an articular finished surface 60 on a substantially dense region 310. This embodiment is similar to the embodiment of FIG. 2A, except that in this embodiment, the transition region 312 is on a portion of the perimeter 311 of the substantially dense region 310 and also between the substantially dense region 310 and a porous region 314. By surrounding a portion of the perimeter 311 of the substantially dense region 310, the transition region 312, which is adapted to be similar to subchondral bone, provides for healing of the native articular cartilage surrounding the monolithic orthopedic implant.

A cross section of another embodiment of the monolithic orthopedic implant is shown in FIG. 2C. This embodiment is similar to FIG. 2B and is for the purpose of illustrating one method of forming the articular surface 320. The substantially dense region 310 or the entire monolithic orthopedic implant 324 may be thermally processed to form the articular surface 320 on top of the substantially dense region 310. The thermal processing may include oxidizing, coating or deposition. Thermal processing of the articular surface may be performed using a laser. For example, when zirconium is thermally processed then zirconia, which is a ceramic, may be formed on the outside of the zirconium to form the articular surface 320 of the monolithic orthopedic implant.

The thermal processing may also form a thin layer 322 on the porous region 314 and the transition region 312; however, this thin layer 322 preferably does not close the pores on or in the porous region 314 and the transition region 312, so that the pores remain open.

The articular surface 320 may be formed by depositing material. For example, pyrolytic carbon or diamond-like carbon may be deposited on the substantially dense region. Yet another method to form the articular surface 320 is coating the substantially dense region with, for example, ceramic or ceramic like material.

Throughout the following description, the embodiments are generally described with reference to the embodiment of FIG. 2A. However, the embodiments of FIGS. 2B and 2C are also applicable to embodiments described below. References to the monolithic orthopedic implant 50 may also refer to the monolithic orthopedic implants of FIGS. 2B and 2C. For example, references to the porous region 56 also refer to porous region 314, and references to the transition region 58 also refer to the transition region 312. References to the substantially dense region 54 also refer to the substantially dense region 310. Similarly, the articular surface 60 may also refer to articular surface 320.

The porous region 56, the transition region 58, the substantially dense region 54 and the surface 60 may have a Vickers hardness of 500 MPa or greater, a nickel content of less than 4%, and a chrome content of less than 10%. Alternatively, the monolithic orthopedic implant 50 may have a substantially dense region 54, which is formed from materials with a Vickers hardness of 1000 MPa or greater and with a bulk porosity of 4% or less. In another embodiment the monolithic orthopedic implant 50 may have a substantially dense region 54, which is formed from materials with a Vickers hardness of 1200 MPa or greater and with a bulk porosity of 0.1% or less.

The substantially dense region 54 may have a composition of materials chosen from the group consisting of oxides, nitrides, carbides or borides, which are all ceramics or any combination thereof. Alternatively, the substantially dense region 54 may include a coated metal selected from oxidized, nitrided-, carburized- or boronized-titanium, zirconium, hafnium, tantalum or molybdenum or any combination thereof. For example, oxidized zirconium forms a coating of zirconia on the outside of the zirconium. One coating that can be used is a thin diamond like coating, which can be polished to the desired very low surface roughness. In another embodiment the substantially dense region 54 may be of a material chosen from the group consisting of partially stabilized zirconia, alumina, silicon nitride or SiAlON or any combination thereof. As discussed above a preferred material for the substantially dense region 54 is partially stabilized zirconia.

The transition region 58 and the porous region 56 may be formed from materials from the group consisting of oxides, carbides, nitrides, or borides or any combination thereof. Alternatively, the transition region 58 and the porous region 56 may be a coated metal comprising oxidized-, nitrided-, carburized- or boronized-titanium, zirconium, hafnium, tantalum or molybdenum. The coated metal is configured for bone ingrowth and is porous. In another embodiment the porous region 56 and the transition region 58 may be formed of materials chosen from the group consisting of partially stabilized zirconia, alumina, silica, silicon nitride, SiAlON, tantalum, titanium, or zirconium or any combination thereof. As discussed above a preferred material for the porous region 56 and the transition region 58 is partially stabilized zirconia.

Another material that may be used for the monolithic orthopedic implant is pyrolytic carbon, a biocompatible material with desirable articular surface properties.

The monolithic orthopedic implant 50 may be used in many joint locations and can be used for a femoral knee prosthesis, a tibial knee prosthesis, a patellar knee prosthesis, a femoral head hip prosthesis, an acetabular hip prosthesis, a finger or thumb prosthesis, a shoulder prosthesis, a toe prosthesis, a spine prosthesis, a wrist or ankle prosthesis, or an elbow prosthesis, among others.

Figure 13B:
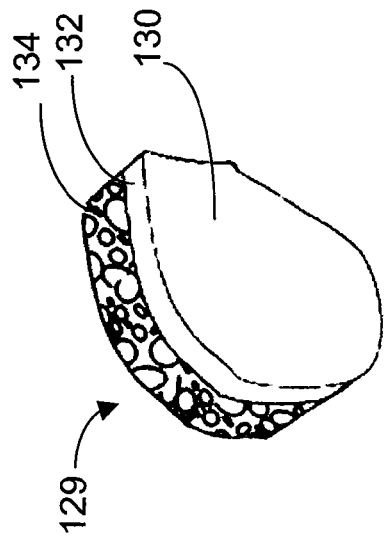
FIG. 13B shows a perspective view of a monolithic orthopedic implant with a porous region and a substantially dense region with an articular surface having a shape to provide a patch in accordance with the present disclosure.
Figure 13D:
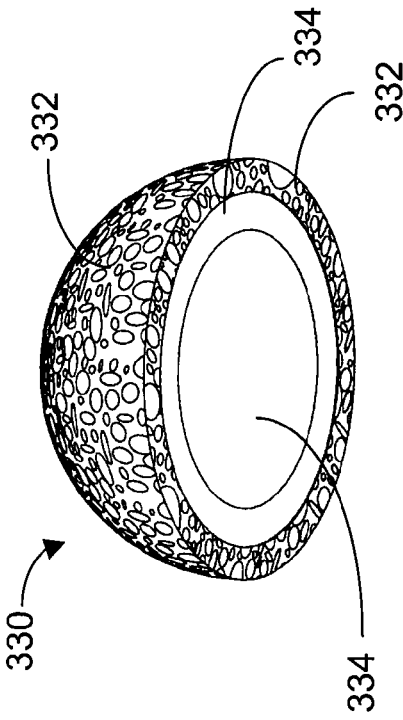
FIG. 13D shows a perspective view of a monolithic orthopedic implant with a porous region on the outside and a substantially dense region having a concave spheroidal shape which can mate with the substantially dense region of FIG. 13C in accordance with the present disclosure.
Figure 13A:
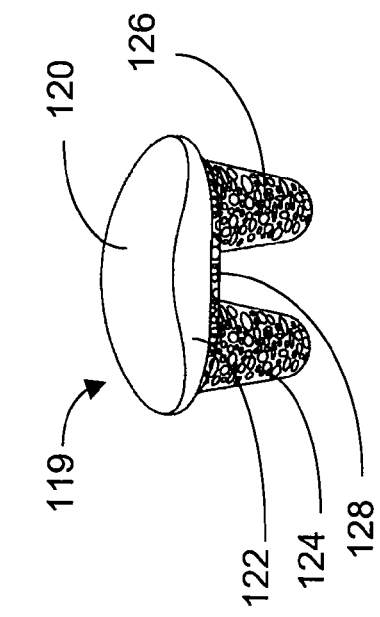
FIG. 13A shows a perspective view of a monolithic orthopedic implant with a porous region with two porous projections and a substantially dense region with an articular surface in accordance with the present disclosure.

To further promote bone ingrowth into the porous region 56, the porous region 56 may have two or more projections, such as shown in FIG. 13A, that are configured to mate with sockets formed in the bone into which the orthopedic implant 50 is implanted.

FIG. 3 shows a perspective view of a monolithic orthopedic implant with the porous region 52, which may include the porous region 56 and the transition region 58, having the shape of a cylindrical plug. In this embodiment the porous region, the transition region and the substantially dense region have approximately the same diameter.

FIG. 4A shows a perspective view of a monolithic orthopedic implant 61 with an articular surface 60 on a substantially dense region 54 and a porous region 62, which may include the porous region 56 and the transition region 58, having the shape of a tapered plug. A tapered porous region has been shown to promote bone ingrowth and may be preferable to a cylindrical plug for some implant conditions.

FIG. 4B shows a variation of the articular surface 60 which has dimples 63 on the substantially dense region 54. Another variation of the articular surface is shown in FIG. 4C which has bumps 67 on the substantially dense region 54. The dimples 63 and the bumps 67 help facilitate hydrostasis in the mating native articular cartilage functioning against the surface of the monolithic implant. The substantially dense region 54 may also have a combination of dimples 63 and bumps 67. The number of dimples or bumps on the surface 60 may be as few as one. Dimples 63 or bumps 67 may also be on the substantially dense region 54 shown in FIG. 3, and on any of the monolithic implant articular surfaces. The dimples 63 and/or bumps 67 serve as examples, and do not limit other protrusion and/or indentation features that can exist on the surface 60 or on the substantially dense region 54 to help facilitate the desired hydrostasis. For example, other protrusion or indentation features may include radial or angled bumps and radial or angled grooves, respectively.

In another embodiment shown in FIG. 4D, in addition to the dimples 63 and/or bumps 67 on the surface 60 of the substantially dense region 54, dimples or bumps 69 may also be on the perimeter of the substantially dense region 54. Dimples or bumps 69 help facilitate hydrostasis in the native articular cartilage surrounding the monolithic implant to aid in healing the articular cartilage that surrounds the perimeter of the substantially dense region 54.

In another embodiment shown in FIG. 4E the dimples or bumps 69 are only on the perimeter of the substantially dense region 54 with no dimples or bumps on the surface 60.

As discussed above, the dimples and bumps 69 serve as examples, and do not limit other protrusion and/or indentation features that can exist on the perimeter of the substantially dense region 54 to help facilitate the desired hydrostasis. For example, other protrusion or indentation features may include radial or angled bumps and radial or angled grooves, respectively.

FIG. 5 shows a perspective view of a monolithic orthopedic implant with the porous region 64 having a tapered shape and a hollow interior 65. The porous region 64 also has an open bottom. In surgery a cylinder or other shape of bone can be removed at the implant site and then the monolithic orthopedic implant of FIG. 5 inserted. Because the monolithic orthopedic implant of FIG. 5 has a hollow interior 65 and open bottom, bone ingrowth can occur from the outside, as well as from the inside of the implant.

In FIG. 5 the porous region 64 is shown as tapered; however, the shape of the porous region in FIG. 5, as well as FIGS. 6, 7A-C, 8A-C, 9A-C, 10A-C, 11A-D, 12A-C, 15A-D and 16A-B may be in the form of a plug or any other shape, including a shape having two or more projections.

Figure 6:
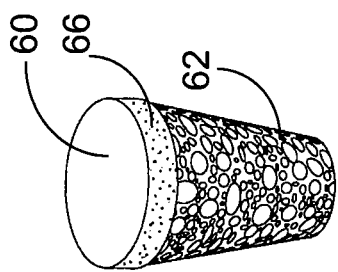
FIG. 6 shows a perspective view of a monolithic orthopedic implant with a porous region and a substantially dense region with a perimeter adapted to promote healing of surrounding articular cartilage in accordance with the present disclosure.

FIG. 6 shows a perspective view of a monolithic orthopedic implant with a porous region 62, which can have any shape, and a substantially dense region with a perimeter 66 adapted to promote healing of surrounding articular cartilage.

In one embodiment the perimeter 66 has a roughness, which may be 6 micrometers $R_a$ or less, to promote healing of surrounding articular cartilage. In another embodiment the perimeter roughness may be greater than 6 micrometers $R_a$.

In another embodiment the perimeter 66 has a hydrophilic surface or a charged surface that influences a cell population to enhance healing of surrounding native articular cartilage. These surface modifications can attract a cell population and/or influence the organization of cells to enhance healing of the surrounding native articular cartilage.

In yet another embodiment the perimeter 66 may include a bioactive mineral coating, which may be hydroxyapatite, bioglass, or a form of calcium phosphate, nonlimiting examples of which are tri-calcium phosphate (TCP), alpha TCP, or beta TCP, or any combination thereof to promote healing of surrounding articular cartilage.

In still another embodiment the perimeter 66 may include a bioengineered coating to promote healing of surrounding articulate cartilage. The bioengineered coating may consist of a blood derived product, such as fibrin glue or fibrin clot, one or more proteins, a peptide, collagen, impregnated autologous chondrocytes, which are cartilage cells, a pharmaceutical agent, or any combination thereof.

The adaptation of the perimeter 66 discussed above in reference to FIG. 6 may also be applied to any of the other embodiments of the monolithic implant described herein, including those implants with bevels or reverse bevels on the substantially dense region.

Figure 7C:
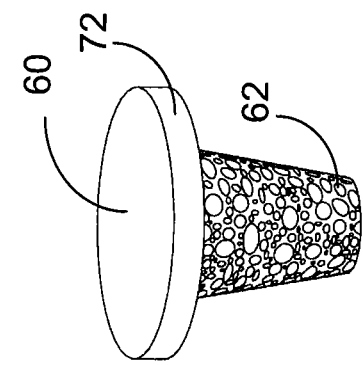
FIG. 7C shows a perspective view of a monolithic orthopedic implant with a porous region and a substantially dense region having size that is relatively larger than the top surface of the porous region in accordance with the present disclosure.
Figure 7B:
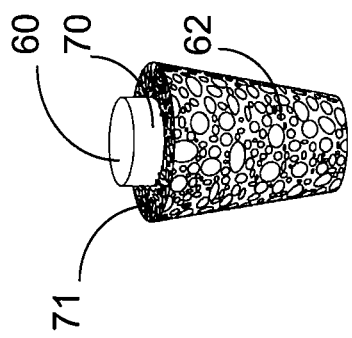
FIG. 7B shows a perspective view of a monolithic orthopedic implant with the porous region and a substantially dense region having size that is relatively smaller than the top surface of the porous region in accordance with the present disclosure.
Figure 7A:
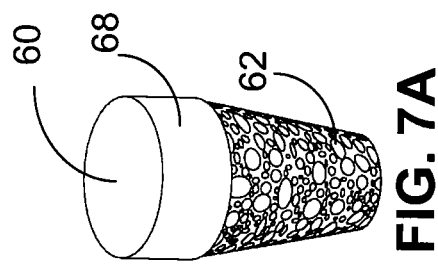
FIG. 7A shows a perspective view of a monolithic orthopedic implant with a porous region and a substantially dense region having a greater thickness to match the thickness of surrounding articular cartilage in accordance with the present disclosure.

FIG. 7A shows a perspective view of a monolithic orthopedic implant with a porous region 62 and a substantially dense region 68 having a relatively greater thickness than the substantially dense region 54 of FIG. 4. The thickness of the substantially dense region 68 is preferably adapted to the thickness of articular cartilage surrounding a particular implant site.

FIG. 7B shows a perspective view of a monolithic orthopedic implant with a porous region 62 and a substantially dense region 70 having a size that is relatively smaller than the top surface 71 of the porous region 62. This embodiment provides an exposed top surface 71 for promoting the healing of surrounding articular cartilage. The exposed top surface 71 of the porous region 62 may have a roughness as described above for the porous region, which may be on the structural members inside porous region 62. The porous region 62, as described above may include a transition region 58. In another embodiment the top surface 71 has a hydrophilic surface or a charged surface that can influence a cell population to enhance healing of surrounding native articular cartilage. The described surface modifications can attract a cell population or influence the organization of cells to enhance healing of the surrounding native articular cartilage.

In yet another embodiment the top surface 71 may include a bioactive mineral coating, which may be hydroxyapatite, bioglass, or a form of calcium phosphate, nonlimiting examples of which are tri-calcium phosphate (TCP), alpha TCP, or beta TCP, or any combination thereof to promote healing of surrounding articular cartilage.

In still another embodiment the top surface 71 may include a bioengineered coating to promote healing of surrounding articulate cartilage. The bioengineered coating may consist of a blood derived product, such as fibrin glue or fibrin clot, one or more proteins, a peptide, collagen, impregnated autologous chondrocytes (cartilage cells), a pharmaceutical agent, or any combination thereof.

FIG. 7C shows a perspective view of a monolithic orthopedic implant with a porous region 62 and a substantially dense region 72 having a size that is relatively larger than the porous region 62 and that overhangs the porous region 62. This configuration allows the amount of bone removed from the implant site to be minimized to implant the porous region 62 into, while providing a large substantially dense region to resurface a large cartilage defect.

FIG. 8A shows a perspective view of a monolithic orthopedic implant with a porous region 62 and a substantially dense region 74 having a polygonal shape, which may be any shape. In FIG. 8A the shape is shown to be a pentagonal shape. FIG. 8B shows a perspective view of a monolithic orthopedic implant with a porous region 62 and a substantially dense region 76 having a hexagonal shape. FIG. 8C shows a perspective view of a monolithic orthopedic implant with a porous region and a substantially dense region 78 having a triangular shape. The polygonal shapes shown in FIGS. 8A-C are especially suitable for clusters of adjacent orthopedic implants as shown in FIG. 14B. Preferably the substantially dense regions in each of these embodiments overlap the porous regions. The clusters of implanted orthopedic implants as shown in FIG. 14B can create a continuous articular surface of a varying contour.

Figure 9B:
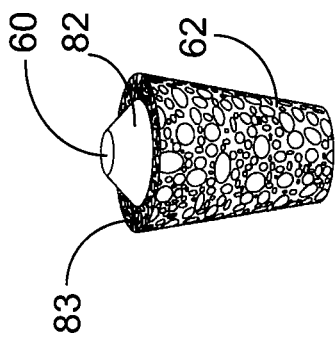
FIG. 9B shows a perspective view of a monolithic orthopedic implant with a porous region and a relatively smaller sized substantially dense region having a beveled perimeter in accordance with the present disclosure.
Figure 9C:
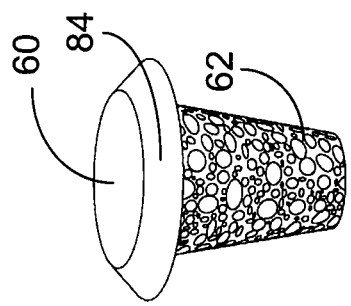
FIG. 9C shows a perspective view of a monolithic orthopedic implant with a porous region and a relatively larger sized substantially dense region having a beveled perimeter in accordance with the present disclosure.
Figure 9A:
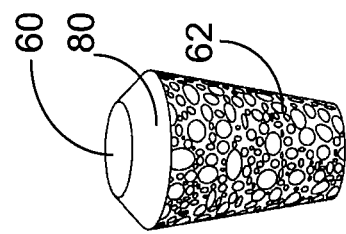
FIG. 9A shows a perspective view of a monolithic orthopedic implant with a porous region and a substantially dense region having a beveled perimeter in accordance with the present disclosure.

FIG. 9A shows a perspective view of a monolithic orthopedic implant with a porous region 62 and a substantially dense region having a beveled perimeter 80. The beveled perimeter 80 may be adapted to provide healing for surrounding native articular cartilage, as discussed in reference to FIG. 6.

FIG. 9B shows a perspective view of a monolithic orthopedic implant with a porous region 62 and a relatively smaller sized substantially dense region with a beveled perimeter 82. In this embodiment the substantially dense region 82 has a dimension less than the top surface 83 of the porous region 62. This embodiment provides the top surface 83 and a beveled perimeter 82 for the surrounding articular cartilage to rest upon. The top surface 83 may be adapted to promote healing of articular cartilage, as discussed with reference to top surface 71 in FIG. 7B. The beveled perimeter 82 may be adapted to provide healing for surrounding native articular cartilage, as discussed above in reference to FIG. 6.

FIG. 9C shows a perspective view of a monolithic orthopedic implant with a porous region 62 and a relatively larger sized substantially dense region having a beveled perimeter 84. In this embodiment the substantially dense region with the beveled perimeter overhangs the porous region 62. The beveled perimeter 84 may be adapted to provide healing for surrounding native articular cartilage, as discussed above in reference to FIG. 6.

Figure 10B:
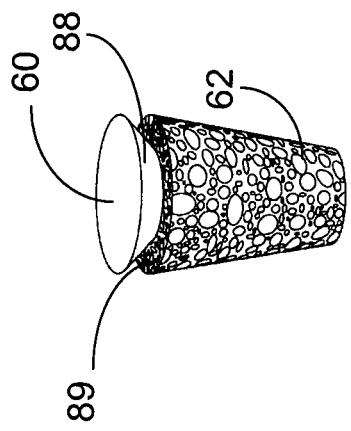
FIG. 10B shows a perspective view of a monolithic orthopedic implant with a porous region and a relatively smaller sized substantially dense region having a reverse bevel perimeter in accordance with the present disclosure.
Figure 10C:
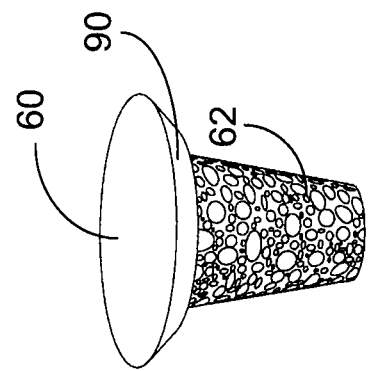
FIG. 10C shows a perspective view of a monolithic orthopedic implant with a porous region and a relatively larger sized substantially dense region having a reverse bevel perimeter in accordance with the present disclosure.
Figure 10A:
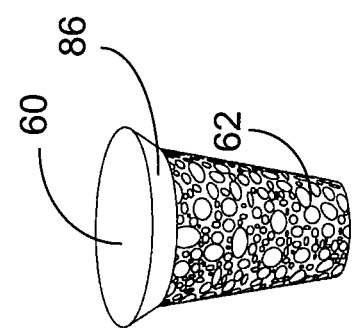
FIG. 10A shows a perspective view of a monolithic orthopedic implant with a porous region and a substantially dense region having a reverse bevel perimeter in accordance with the present disclosure.

FIG. 10A shows a perspective view of a monolithic orthopedic implant with a porous region 62 and a substantially dense region having a reverse bevel perimeter 86 which provides a surface to protect the so-called tidemark region of the surrounding native articular cartilage, where the surrounding native articular cartilage joins to the subchondral bone, from experiencing damaging shear stresses. The reverse bevel 86 may have a perimeter adapted to promote healing of articular cartilage, as discussed for FIG. 6.

FIG. 10B shows a perspective view of a monolithic orthopedic implant with a porous region 62 and a relatively smaller sized substantially dense region having a reverse bevel perimeter 88. In this embodiment the substantially dense region has a dimension less than the top surface 89 of the porous region 62. This embodiment provides the top surface 89 for the surrounding articular cartilage to rest upon and the reverse bevel perimeter 88 provides a surface to protect the tidemark region of the surrounding native articular cartilage from experiencing damaging shear stresses. The top surface 89 may be adapted to promote healing of articular cartilage, as discussed with reference to top surface 71 in FIG. 7B. The reverse bevel 88 on the perimeter may be adapted to provide healing for surrounding native articular cartilage, as discussed in reference to FIG. 6.

FIG. 10C shows a perspective view of a monolithic orthopedic implant with a porous region 62 and a relatively larger sized substantially dense region having a reverse bevel perimeter 90 that provides a surface to protect the tidemark region of the surrounding native articular cartilage from experiencing damaging shear stresses. The substantially dense region overhangs the porous region 62. The reverse bevel 90 on the perimeter may be adapted to provide healing for surrounding native articular cartilage in the same manner as discussed for FIGS. 10A and 10B.

Figure 11A:
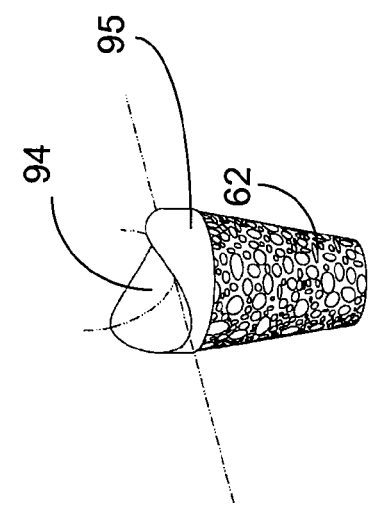
FIG. 11A shows a perspective view of a monolithic orthopedic implant with a porous region and a substantially dense region with an articular surface having a relative concave spherical shape to match a skeletal joint in accordance with the present disclosure.
Figure 11B:
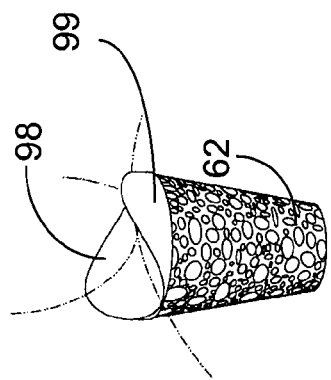
FIG. 11B shows a perspective view of a monolithic orthopedic implant with a porous region and a substantially dense region with an articular surface having a relative concave shape with a radius in one plane to match a skeletal joint in accordance with the present disclosure.
Figure 11C:
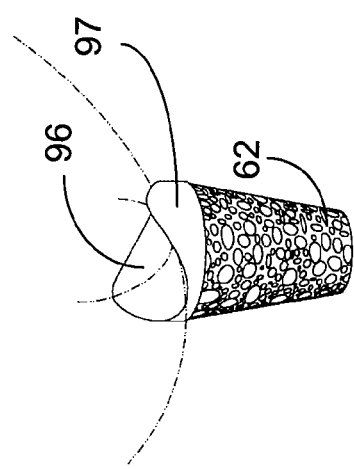
FIG. 11C shows a perspective view of a monolithic orthopedic implant with a porous region and a substantially dense region with an articular surface having a relative concave shape with two differing radii in two planes to match a skeletal joint in accordance with the present disclosure.
Figure 11D:
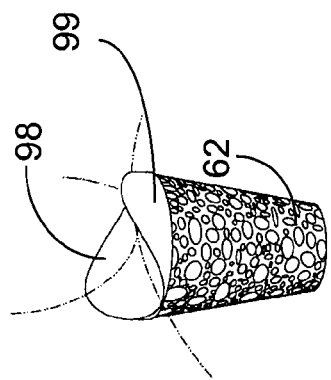
FIG. 11D shows a perspective view of a monolithic orthopedic implant with a porous region and a substantially dense region with an articular surface having a concave shape in one plane and a convex shape in another plane to match a skeletal joint in accordance with the present disclosure.

To match the curvature of a joint, the surface of the substantially dense region may have the following embodiments. Note that the following surface curvatures may be applied to many implant configurations, including those with substantially dense regions smaller or larger than the porous region and those with beveled or reverse beveled perimeters. FIG. 11A shows a perspective view of a monolithic orthopedic implant with a porous region 62 and a substantially dense region 93 with an articular surface 92 having a relative concave spherical shape to match a skeletal joint. FIG. 11B shows a perspective view of a monolithic orthopedic implant with a porous region 62 and a substantially dense region 95 with an articular surface 94 having a relative concave shape with a radius in one plane to match a skeletal joint. FIG. 11C shows a perspective view of a monolithic orthopedic implant with a porous region 62 and a substantially dense region 97 with an articular surface 96 having a relative concave shape with two differing radii in two orthogonal planes to match a skeletal joint. FIG. 11D shows a perspective view of a monolithic orthopedic implant with a porous region 62 and a substantially dense region 99 with an articular surface 98 having a concave shape in one plane and a convex shape in another plane to match a skeletal joint.

FIG. 12A shows a perspective view of a monolithic orthopedic implant with a porous region 62 and a substantially dense region 100 with an articular surface 101 having a convex spherical shape to match a skeletal joint. FIG. 12B shows a perspective view of a monolithic orthopedic implant with a porous region 62 and a substantially dense region 102 with an articular surface 103 having a convex shape with a radius in one plane to match a skeletal joint. FIG. 12C shows a perspective view of a monolithic orthopedic implant with a porous region 62 and a substantially dense region 104 with an articular surface 105 having a convex shape with two differing radii in two orthogonal planes to match a skeletal joint.

The monolithic orthopedic implant 50 can be fabricated as shown in FIG. 17 by forming in step 200 a porous region 56 having an interconnected porous form adapted to be similar to cancellous bone to promote skeletal fixation by bone ingrowth of cancellous bone, forming in step 202 a transition region 58 adjacent to and integrally joined to the porous region 56, the transition region 58 adapted to be similar to subchondral bone, forming in step 204 a substantially dense region 54 integrally joined to the transition region 58, and forming in step 206 a surface 60 on the substantially dense region 54, the surface 60 having a finish adapted for articulation against native articular cartilage. The porous region is preferably formed with a porosity gradient that increases as a distance from the substantially dense region 54 increases as shown in step 208. Also, preferably, the formed monolithic orthopedic implant is non-resorbable as shown in step 210.

The articular surface on the substantially dense region may be formed by thermally processing the substantially dense region or the entire monolithic orthopedic implant as shown in step 212 of FIG. 17. Thermal processing may include oxidation, coating or deposition of material. The material deposited on the substantially dense region may include pyrolytic carbon, diamond, or diamond-like carbon. Yet another method for forming the articular surface includes coating a material on the substantially dense region, such as ceramic or ceramic like material.

The porosity of the porous region 56 and the transition region 58 may be formed by oxidizing a fugitive material, dissolving a fugitive material, using a lost foam process, using a solid freeform fabrication process, or using a foaming process, which are processes well known in the art.

The orthopedic implant 50 may be formed into a desired geometrical form by milling, turning or other machining processes. Preferably these processes are adjusted to account for any shrinkage that may occur during milling, turning or other machining processes. Such shrinkage can be 10% or greater.

FIG. 13A shows a perspective view of a monolithic orthopedic implant 119 with a porous region with two porous projections 124 and 126, a transition region 128 and a substantially dense region 122 with a surface 120 for articulation with articular cartilage on an opposing joint. The projections, which may number more than two, increase the surface area of the porous region, which further promotes bone ingrowth, to provide a secure attachment of the monolithic orthopedic implant 50.

FIG. 13B shows a perspective view of a monolithic orthopedic implant 129 with a porous region 134 and a substantially dense region 132 with an articular surface 130 having a shape having different dimensions in orthogonal planes for a regional implant. The irregular shape of monolithic orthopedic implant 129 can be adjusted to fit the circumstances required for an implant. The porous region 134 may have a tapered perimeter.

Figure 13C:
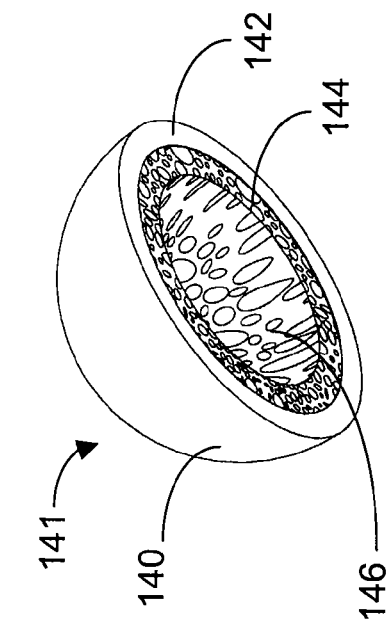
FIG. 13C shows a perspective view of a monolithic orthopedic implant with a porous region on the inside and a substantially dense region having a shell like shape characteristic of a spheroidal skeletal joint in accordance with the present disclosure.

FIG. 13C shows a perspective view of a monolithic orthopedic implant 141 in a shell like shape with a porous region 144 and a substantially dense region 142. The shell like shape is characteristic of a spheroidal skeletal joint. The substantially dense region 142 has a shell like shape and the porous region 144 has a shell-like shape with a hollow interior 146 for bone ingrowth.

FIG. 13D shows a perspective view of a monolithic orthopedic implant 330 with a porous region 332 on the outside of the implant 330 and a concave substantially dense region 334. The monolithic orthopedic implant 330 can be used alone or be implanted so that the concave substantially dense region 334 mates with the spheroidal substantially dense region 142 of FIG. 13C.

Figure 14A:
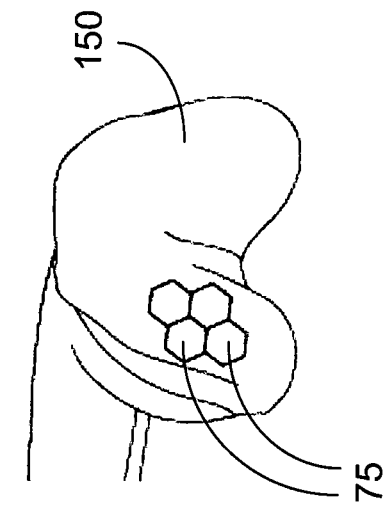
FIG. 14A shows a perspective view of the monolithic orthopedic implant of FIG. 4A implanted in a femur bone to provide a repair for native articular cartilage on the bone in a skeletal joint in accordance with the present disclosure.
Figure 14B:
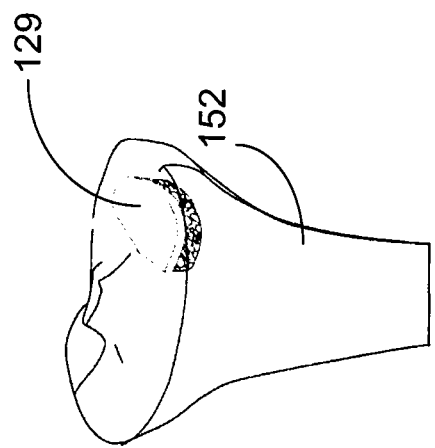
FIG. 14B shows a perspective view of a plurality of the monolithic orthopedic implants of FIG. 8B implanted in a femur bone adjacent to one another to create a continuous articular surface of a varying contour to provide a repair for native articular cartilage on the bone in a skeletal joint in accordance with the present disclosure.
Figure 14C:
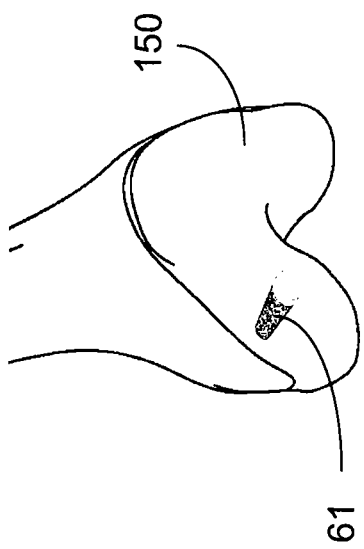
FIG. 14C shows a perspective view of the monolithic orthopedic implant of FIG. 13A implanted in a femur bone to provide a repair for native articular cartilage on the bone in a skeletal joint in accordance with the present disclosure.
Figure 14D:
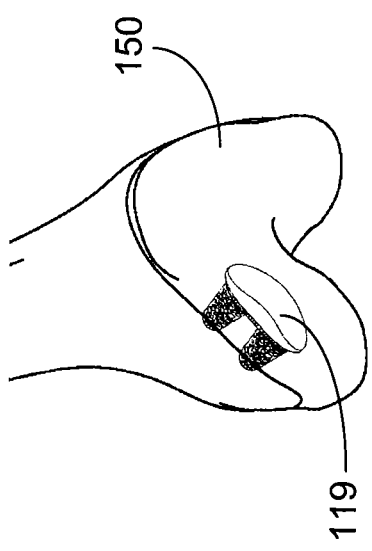
FIG. 14D shows a perspective view of the monolithic orthopedic implant of FIG. 13B implanted in a tibial bone to provide a repair for native articular cartilage on the bone end in a skeletal joint in accordance with the present disclosure.

FIGS. 14A to 14D show examples of the orthopedic implant in use for a knee prosthesis. FIG. 14A shows a perspective view of the monolithic orthopedic implant 61 of FIG. 4A implanted in a femur bone 150 to provide a repair for native articular cartilage. FIG. 14B shows a perspective view of a plurality of the monolithic orthopedic implants 75 of FIG. 8B implanted in a femur bone 150 adjacent to one another to create a continuous articular surface of a varying contour to provide a repair for native articular cartilage on the femur bone 150. FIG. 14C shows a perspective view of the monolithic orthopedic implant 119 of FIG. 13A implanted in a femur bone. FIG. 14D shows a perspective view of the monolithic orthopedic implant 129 of FIG. 13B implanted in a tibial bone.

In an orthopedic surgery method to implant the monolithic orthopedic implant 50, a portion of articular cartilage at an implant site may be removed, as shown in FIG. 18A step 220. Then a socket is formed also in step 220 in bone underlying the removed articular cartilage. The socket should be formed to have a depth such that the surface of the substantially dense region of the monolithic implant is approximately flush to the articular cartilage at the implant site. Next the orthopedic implant 50, and in particular the porous region 56 of the orthopedic implant 50, are implanted into the socket in step 220. The implanted monolithic orthopedic implant includes a porous region having a form of interconnected porosity adapted to be similar to cancellous bone to promote skeletal fixation by bone ingrowth, a transition region having a form of interconnected porosity similar to subchondral bone and interconnected to the porous region, a substantially dense region integrally joined to the transition region, and a surface on the substantially dense region, the surface having a finish adapted for articulation against native articular cartilage as shown in step 222 of FIG. 18A. Preferably the porous region has a porosity gradient that increases as a distance from the substantially dense region increases, as shown in step 224 of FIG. 18A, and the porous region, the transition region, the substantially dense region, and the surface are non-resorbable as shown in step 226 of FIG. 18A. As shown in step 228 of FIG. 18A the porous region, the transition region, the substantially dense region, and the surface may comprise ceramic.

In one embodiment the method for implanting includes implanting a plurality of monolithic orthopedic implants adjacent to one another to create a nearly continuous articular surface, which can have a varying contour to match the curvature of a joint, as shown in FIG. 14B, and as shown in step 232 of FIG. 18B. In this embodiment, the substantially dense region of each monolithic orthopedic implant has a polygon shaped perimeter, as shown in step 232 of FIG. 18B, and FIGS. 8A-8C.

In one embodiment removing a portion of the articular cartilage at the implant site includes preparing the implant site by excising the portion of the articular cartilage to form a predetermined geometrical lesion and forming at the implant site a socket in the bone conforming geometrically to a form of the orthopedic implant. The dimensions of the socket preferably allow for a compressive or interference fit between the bone and the orthopedic implant 50. Also two or more sockets may be formed at the implant site if the orthopedic implant 50 has multiple projections, as shown in FIG. 13A and 14C. Preferably the sockets have conical dimensions.

In another embodiment, shown in FIG. 15A, an orthopedic implant 160 has a porous region 162 and a transition region 164. The porous region 162 is adapted to have a form of porosity similar to cancellous bone to promote bone ingrowth to securely implant the orthopedic implant 160 in a bone. The transition region 164 is adapted to have a form of porosity similar to subchondral bone. The porous region 162 and the transition region 164 are preferably non-resorbable.

A scaffold 166 adapted to promote regeneration of the surrounding articular cartilage may be coupled to the transition region 164, and FIG. 15B shows the scaffold 166 coupled to the transition region 164. The scaffold 166 may include collagen, one or more proteins, a resorbable material, copolymer resorbable material, a mineral, hydrogel, living cells, or articular cartilage or any combination thereof. Examples of resorbable materials that can be used for the matrix are polylactic acid (PLA), which is a biodegradable, thermoplastic, aliphatic polyester, polyglycolic acid (PGA), which is a biodegradable, thermoplastic polymer.

The transition region 164 may be further adapted to promote regeneration of articular cartilage. In one embodiment the transition region has a roughness, which may be on the outside of the transition region 164 and also on the inside of the transition region 164. Preferably the transition region includes a three dimensional framework of interconnected structural members with interstitial interconnected passages there between and the roughness may be on the structural members.

In another embodiment the transition region 164 has a hydrophilic surface or a charged surface that can influence a cell population to enhance healing of surrounding native articular cartilage. These surface modifications can attract a cell population and/or influence the organization of cells to enhance healing of the surrounding native articular cartilage.

In yet another embodiment the transition region 164 may include a bioactive mineral coating, which may be hydroxyapatite, bioglass, or a form of calcium phosphate, nonlimiting examples of which are tri-calcium phosphate (TCP), alpha TCP, or beta TCP, or any combination thereof to promote healing of surrounding articular cartilage.

In still another embodiment the transition region 164 may include a bioengineered coating to promote healing of the articulate cartilage. The bioengineered coating may consist of a blood derived product, such as fibrin glue or fibrin clot, one or more proteins, a peptide, collagen, impregnated autologous chondrocytes (cartilage cells), or any combination thereof.

The porous region 162 also may be further adapted to promote bone ingrowth for bone fixation. In one embodiment the porous region 162 has a roughness, characterized by a frictional coefficient similar to cancellous bone, which is generally greater than 0.5. The frictional coefficient is a biomechanical characterization of friction between cancellous bone and cortical bone. The frictional coefficient of the porous region 162 helps prevent the formation of a fibrous layer, which can retard bone ingrowth. The roughness may be on the outside of the porous region 162 and also on the inside of the porous region 162. The porous region 162 is preferably a three dimensional framework of interconnected structural members with interstitial interconnected passages there between and the roughness may be on the structural members, which provides a microstructure to promote bone ingrowth and fixation by facilitating cell adhesion.

In another embodiment the porous region 162 may also have a hydrophilic or a charged surface that can influence a cell population to enhance healing of surrounding native articular cartilage. The described surface modifications can attract a cell population or influence the organization of cells to enhance healing of the surrounding native articular cartilage.

In yet another embodiment the porous region 162 may include a bioactive mineral coating, which may be hydroxyapatite, bioglass, or a form of calcium phosphate, nonlimiting examples of which are tri-calcium phosphate (TCP), alpha TCP or beta TCP, or any combination thereof to promote bone ingrowth for bone fixation.

In still another embodiment the porous region 162 may include a bioengineered coating to promote bone ingrowth for bone fixation. The bioengineered coating may consist of one or more proteins, a peptide, or any combination thereof.

As shown in FIG. 15C the orthopedic implant, as discussed with reference to FIGS. 15A and 15B, may have a porous region 170 with a hollow interior 172 and have an open bottom to promote bone ingrowth from the inside, as well as the outside of the implant.

FIG. 15D shows a perspective view of a dental implant 174 with a porous region 175 integrally joined to a substantially dense region 176 having a surface 177 and a perimeter 178 adapted to be compatible with gum tissue in ways well known in the art. The porous region 175 promotes bone ingrowth to firmly attach the implant to the bone and the substantially dense region may be used to attach a tooth. Because the surface 177 and the perimeter 178 are compatible with gum tissue the implant is well adapted for a dental implant.

FIG. 16A shows a perspective view of a monolithic non-resorbable porous implant 180, which has a porous top surface 181. This embodiment can be used as a bone patch among other possible uses. In one embodiment the implant may be adapted to restore the metaphyseal region in the end of a long bone making up a skeletal joint. FIG. 16B shows a perspective view of a monolithic non-resorbable porous implant 182, which has an open top 184 and a hollow interior 185.

The porous implants 180 and 182 have a three dimensional framework of structural members with interstitial interconnected passages between the structural members. The material of the framework is preferably non-resorbable ceramic, and each structural member may be similar in size to a trabecula in bone.

The interconnected pore passageways may each have a dimension less than 1000 micrometers or each have a dimension between 200 and 600 micrometers. The framework may have a bulk porosity of 50% or greater.

The porous implants 180 and 182 of FIG. 16A and FIG. 16B, respectively, may be further adapted to promote bone ingrowth for bone fixation in the same manner as the porous region 162 of FIGS. 15A and 15B, as discussed above. The implants 180 and 182 may have a roughness to promote bone ingrowth for bone fixation and the roughness may be characterized by a frictional coefficient greater than 0.5.

To promote bone ingrowth, each structural member may have a roughness. In another embodiment to promote bone ingrowth, the framework may have a hydrophilic coating or a charged coating, which as discussed above can attract a cell population and/or influence the organization of cells to enhance healing of the surrounding native articular cartilage.

In another embodiment, the framework may have a bioactive mineral coating, which can be hydroxyapatite, bioglass, or a form of calcium phosphate or any combination thereof. In another embodiment the framework has a bioengineered coating one or more proteins or a peptide or any combination thereof.

The implants 180 and 182 may be formed from materials from the group consisting of oxides, carbides, nitrides, or borides or any combination thereof. Alternatively, the implants may be formed of coated metal consisting of oxidized-, nitrided-, carburized- or boronized-titanium, zirconium, hafnium, tantalum, or molybdenum or any combination thereof. The framework may also be formed of materials chosen from the group consisting of partially stabilized zirconia, alumina, silica, silicon nitride, SiAlON, tantalum, titanium, or zirconium or any combination thereof.

Brittle materials, such as ceramics, usually have lower and less reliable strength values compared to ductile materials, such as metals. The reduced reliability of the strength values of brittle material is due primarily to voids or defects present inside the material, which may result from the process of forming the material from raw material powder. It is desirable to improve the reliability of strength values of these brittle materials, so that brittle materials can be used reliably in devices to surgically treat skeletal joint conditions such as arthritis and cartilage lesions.

Flaws in brittle materials are generally statistical in nature. As such, the strength value of a brittle material is not one specific value, but a distribution of strength values. For brittle materials, the maximum strength, or the maximum stress that a sample can withstand, may vary unpredictably from specimen to specimen, even under identical testing conditions. The strength of a brittle material is thus more completely described with a statistical measure of this variability. The Weibull modulus is a measure of the distribution of the strength values, and is a dimensionless number corresponding to the variability in strength values and generally reflects the distribution of flaws in the material.

For example, consider strength measurements made on many specimens of a brittle material, such as ceramic. If the measurements show little variation from specimen to specimen, the Weibull modulus will be high and the average strength of the material is therefore a good representation of the potential specimen to specimen performance of the material. A material with a high Weibull modulus is consistent and any flaws, due to the material itself and/or the manufacturing process for the material, are distributed uniformly and finely throughout the material. A low Weibull modulus reflects a high variation in measured strengths and an indication that the likelihood is increased that flaws in the material tend to congregate and thereby produce some specimens that are quite weak compared to the average strength of a set of specimens of the material. Thus, a material with a low Weibull modulus will more likely produce products with a strength substantially below the average and show greater inconsistency of strength. Such products will exhibit greater variation in strength performance and are therefore be less reliable.

Brittle material specimens of ceramic materials were structurally tested to obtain their Weibull modulus. The first material specimens tested were ceramic specimens that were porous, and which corresponded to the porous regions 52 of monolithic orthopedic implant 50. These porous ceramic specimens had a high variability in strength and a Weibull modulus of 3.6. The second material specimens tested were ceramic specimens that were relatively solid or substantially dense, and which corresponded to the substantially dense region 54 of monolithic orthopedic implant 50. These relatively solid ceramic specimens had a low variability in strength and a Weibull modulus of 8.4.

Next specimens were tested of a monolithic material having a porous ceramic region integrally joined to a relatively solid or substantially dense ceramic region. The porous ceramic region was formed to be similar to the porous ceramic specimens with a Weibull modulus of 3.6, and the relatively solid ceramic or substantially dense region was formed to be similar to the relatively solid ceramic specimens with a Weibull modulus of 8.4. These monolithic material specimens were found to have a Weibull modulus of 22.2, which indicates that the monolithic specimens had little variation in strength from specimen to specimen, and therefore the average strength of the monolithic material is a good representation of the potential specimen to specimen performance of the material. The high Weibull modulus also indicates that the monolithic material is more reliable than either the porous ceramic region or the relatively solid region of substantially dense material by themselves.

The monolithic material Weibull modulus is surprising, because those not knowing this result would consider that the strength reliability of the monolithic material would fall between that of the porous specimens and the relatively solid or substantially dense specimens, or in any case be not more than the relatively solid specimens.

One possible technical explanation of this surprising result is "crack blunting" or "crack dissipation" wherein a stress concentration (defect) is counteracted by a compressive force, at the grain level. Another possible technical explanation relates to crack deviation, where multiple small cracks collectively distribute stress within the material developing a characteristic known as micro crack toughening.

In another embodiment of the monolithic material there may be a transition region between and integrally joined to the porous region and the relatively solid region. The transition region, which may correspond to transition region 58 of monolithic orthopedic implant 50, may have a porosity that is relatively lower than the porosity of the porous region and varies between the relatively solid region and the porous region. In this embodiment the Weibull modulus for the monolithic material is higher than for the porous region, the transition region, or the relatively solid region by themselves, which again is a surprising result.

The brittle materials that may be used to form the monolithic materials include materials chosen from the group consisting of oxides, nitrides, carbides or borides or any combination thereof, which are all ceramics, materials chosen from the group consisting of partially stabilized zirconia, alumina, silica, silicon nitride or SiAlON or any combination thereof, and pyrolytic carbon. These are all brittle materials and a monolithic material formed of any of these materials and having a porous region integrally joined to a relatively solid region, or having a transition region between the porous region and the relatively solid region has a higher Weibull modulus and therefore greater strength reliability from specimen to specimen than either the porous region or the relatively solid region by themselves.

Because the monolithic material has improved strength value reliability, the monolithic materials are suitable and can be used to develop reliable devices to surgically treat skeletal joint conditions such as arthritis and cartilage lesions. The orthopedic devices made of the monolithic material may include any of the monolithic orthopedic implants described herein and shown throughout the figures, as well as other orthopedic devices. As described herein, a monolithic device that has integrally joined porous, transition and substantially dense regions has advantages for many types of orthopedic implants and devices.

FIG. 19 is a flow diagram of a method for providing a monolithic material in accordance with the present disclosure. In step 240 a porous region is formed having a first variability of strength. A substantially dense region is formed and joined in step 242 to the porous region, the substantially dense region having a second variability of strength, wherein the variability of strength of the monolithic material is less than the first and second variability of strengths.

In step 244 a transition region is formed between the porous region and the substantially dense region and joined to the porous region and the substantially dense region, the transition region having a third variability of strength, wherein the variability of strength of the monolithic material is also less than the third variability of strength. The transition region may be formed on the porous region or the substantially dense region and then the substantially dense region or the porous region formed on the transition region, respectively.

In step 246 a surface may be formed on the substantially dense region, the surface having a finish adapted for articulation against native articular cartilage.

FIG. 20 is another flow diagram of a method for providing a monolithic material in accordance with the present disclosure. In step 250, a first region is formed having a first variability of strength. In step 252 a second region is formed and joined to the first region, the second region having a second variability of strength, wherein the monolithic material has a variability of strength less than the first variability of strength of the first region and less than the second variability of strength of the second region. Then in step 254 a third region may be formed between and joined to the first region and the second region, the third region having a third variability of strength, wherein the variability of strength of the monolithic material is less than the third variability of strength of the third region.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . "

What is claimed is:

1. A monolithic orthopedic implant made entirely of a brittle, non-resorbable, monolithic material and having an overall implant variability of strength measured as an overall implant Weibull Modulus, the implant comprising:
   a porous region having a first variability of strength measured as a first Weibull Modulus;
   a transition region located over and integrally joined to the porous region and having a second variability of strength measured as a second Weibull Modulus, wherein the second variability of strength is less than the first variability of strength, and wherein the second Weibull Modulus is greater than the first Weibull Modulus;
   a dense region located over and integrally joined to the transition region and having a third variability of strength measured as a third Weibull Modulus, wherein the third variability of strength is less than the second variability of strength, and wherein the third Weibull Modulus is greater than the second Weibull Modulus; and
   a surface on top of the dense region, the surface having a finish adapted for articulation against native articular cartilage;
   wherein the overall implant variability of strength is less than the third variability of strength, and wherein the overall implant Weibull Modulus is greater than the third Weibull Modulus.

2. The monolithic orthopedic implant of claim 1 wherein the porous region has a bulk porosity of at least 50 percent, wherein the dense region has a bulk porosity of 4 percent or less, and wherein the transition region has a bulk porosity that is between the bulk porosities of the porous and dense regions.

3. The monolithic orthopedic implant of claim 1, wherein the brittle, non-resorbable, monolithic material is selected from the group consisting of oxides, nitrides, carbides, borides, partially stabilized zirconia, alumina, silica, silicon nitride, SiAlON, and pyrolytic carbon.

4. The monolithic orthopedic implant of claim 1, wherein the porous region has a porosity gradient that increases as a distance from the dense region increases.

5. The monolithic orthopedic implant of claim 1, wherein the porous region, the transition region, the dense region, and the surface have a Vickers hardness of 500 MPa or greater, a nickel content of less than 4%, and a chrome content of less than 10%.

6. The monolithic orthopedic implant of claim 1, wherein the dense region has a Vickers hardness of 1000 MPa or greater and a bulk porosity of 4% or less.

7. The monolithic orthopedic implant of claim 1, wherein the surface is finished to a roughness of 6 micrometers $R_a$ or less.

8. The monolithic orthopedic implant of claim 1, wherein the surface is finished to a roughness of 0.025 micrometers $R_a$ or less.

9. The monolithic orthopedic implant of claim 1, wherein the porous region comprises a three dimensional framework of structural members with interstitial interconnected passages therebetween.

10. The monolithic orthopedic implant of claim 1, wherein the porous region has interconnected pore passageways, each having a diameter less than 1000 micrometers.

11. The monolithic orthopedic implant of claim 1, wherein the porous region has interconnected pore passageways each, having a diameter between 200 and 600 micrometers.

12. The monolithic orthopedic implant of claim 1 wherein the porous region has a bulk porosity of 50% or greater.

13. The monolithic orthopedic implant of claim 1 wherein the transition region has a relatively lower porosity than the porous region to provide strength and to support capillary movement of fluid between cancellous bone and articular cartilage.

14. The monolithic orthopedic implant of claim 1, wherein a perimeter of the dense region comprises a roughness of 6 micrometers $R_a$ or greater.

15. The monolithic orthopedic implant of claim 1, wherein the porous region comprises roughness characterized by a frictional coefficient greater than 0.5.

16. The monolithic orthopedic implant of claim 1 wherein the porous region comprises a hydrophilic surface.

17. The monolithic orthopedic implant of claim 1 wherein the porous region comprises a charged surface.

18. The monolithic orthopedic implant of claim 1 wherein the porous region comprises a bioactive mineral coating to promote bone ingrowth for bone fixation.

19. The monolithic orthopedic implant of claim 18, wherein the bioactive mineral coating is selected from the group consisting of hydroxyapatite, bioglass, calcium phosphate, and any combination thereof.

20. The monolithic orthopedic implant of claim 1 wherein the porous region comprises a bioengineered coating to promote bone ingrowth for bone fixation.

21. The monolithic orthopedic implant of claim 20, wherein the bioengineered coating is selected from the group consisting of a protein, a peptide, and any combination thereof.

22. The monolithic orthopedic implant of claim 1, wherein the dense region has a first thickness matching a second thickness of surrounding native articular cartilage.

* * * * *